United States Patent
Johns et al.

(10) Patent No.: US 10,709,668 B2
(45) Date of Patent: Jul. 14, 2020

(54) SPRINKLE FORMULATIONS OF ACAMPROSATE

(71) Applicant: CONFLUENCE PHARMACEUTICALS, LLC, Carmel, IN (US)

(72) Inventors: Steven L. Johns, Carmel, IN (US); Kenneth G. Payie, Poway, CA (US); Badrinath R. Doniparthi, Bengaluru (IN); Shivaraj B. Munianjanappa, Bengaluru (IN)

(73) Assignee: CONFLUENCE PHARMACEUTICALS, LLC, Carmel, IN (US)

( * ) Notice: Subject to any disclaimer, the term of this patent is extended or adjusted under 35 U.S.C. 154(b) by 0 days.

(21) Appl. No.: 15/569,937

(22) PCT Filed: May 4, 2016

(86) PCT No.: PCT/US2016/030725
§ 371 (c)(1),
(2) Date: Oct. 27, 2017

(87) PCT Pub. No.: WO2016/179252
PCT Pub. Date: Nov. 10, 2016

(65) Prior Publication Data
US 2019/0046458 A1    Feb. 14, 2019

Related U.S. Application Data

(60) Provisional application No. 62/260,161, filed on Nov. 25, 2015, provisional application No. 62/156,842, filed on May 4, 2015.

(51) Int. Cl.
| | | |
|---|---|---|
| *A61K 9/50* | (2006.01) | |
| *A61K 31/185* | (2006.01) | |
| *A61K 9/00* | (2006.01) | |
| *A61P 25/28* | (2006.01) | |
| *A61K 9/48* | (2006.01) | |

(52) U.S. Cl.
CPC ............ *A61K 9/5073* (2013.01); *A61K 9/009* (2013.01); *A61K 9/0056* (2013.01); *A61K 9/4808* (2013.01); *A61K 9/5026* (2013.01); *A61K 9/5047* (2013.01); *A61K 31/185* (2013.01); *A61P 25/28* (2018.01); *A61K 9/4866* (2013.01)

(58) Field of Classification Search
CPC .... A61K 31/185; A61K 9/0056; A61K 9/009; A61K 9/4808; A61K 9/4866; A61K 9/5026; A61K 9/5047; A61K 9/5073; A61P 25/28
See application file for complete search history.

(56) References Cited

U.S. PATENT DOCUMENTS

| | | |
|---|---|---|
| 2002/0006439 A1 | 1/2002 | Skluzacek |
| 2002/0035145 A1 | 3/2002 | Tsai et al. |
| 2005/0042277 A1* | 2/2005 | Srinivas ............... A61K 9/2886 424/452 |
| 2008/0206324 A1 | 8/2008 | Gryczke |
| 2010/0216805 A1 | 8/2010 | Barlow et al. |
| 2011/0142889 A1 | 6/2011 | Lee et al. |
| 2012/0016036 A1 | 1/2012 | Erickson |
| 2012/0077878 A1* | 3/2012 | Berner ................. A61K 9/0065 514/578 |
| 2013/0143867 A1 | 6/2013 | Fogel et al. |
| 2014/0378440 A1 | 12/2014 | Cohen |
| 2016/0354335 A1 | 12/2016 | Cohen |

FOREIGN PATENT DOCUMENTS

| | | |
|---|---|---|
| EP | 2727473 | 5/2014 |
| WO | 2009004082 | 1/2009 |
| WO | 2014197744 | 12/2014 |
| WO | 2016179252 | 11/2016 |

OTHER PUBLICATIONS

Grados, Marco A., et al. "Glutamate drugs and pharmacogenetics of OCD: a pathway-based exploratory approach." Expert opinion on drug discovery 8.12 (2013): 1515-1527.
Olive, M. Foster, et al. "Glutamatergic medications for the treatment of drug and behavioral addictions." Pharmacology Biochemistry and Behavior 100.4 (2012): 801-810.
PCT Search Report prepared for PCT/US2016/030725, dated Aug. 5, 2016.
Material Safety Data Sheet Avicel® PH Microcrystalline Cellulose, FMC BioPolymer, Jan. 31, 2009, 9 pages.
Ethocel premium polymers for pharmaceutical applications, Dow, Oct. 1998, 9 pages.
PCT Search Report prepared for PCT/US2016/045547, dated Oct. 26, 2016.
El-Ansary, A., & Al-Ayadhi, L. (2014). GABAergic/glutamatergic imbalance relative to excessive neuroinflammation in autism spectrum disorders. Journal of neuroinflammation, 11(1), 189.
"Eudragit", Dec. 2012, Eudragit, pp. 107.
PCT Search Report prepared for PCT/US2018/033205, dated Aug. 10, 2018.

* cited by examiner

*Primary Examiner* — Michael B. Pallay
(74) *Attorney, Agent, or Firm* — Brannon Sowers & Cracraft PC

(57) ABSTRACT

The present invention provides an orally-administrable, pharmaceutical formulation comprising: a plurality of pellets, wherein: the pellets comprise a core, a sustained release coating, and an enteric coating; and the core comprises an active ingredient and a diluent.

20 Claims, 12 Drawing Sheets

FIGURE 1: Dissolution profile of acamprosate calcium enteric-coated sprinkles (#25/30)
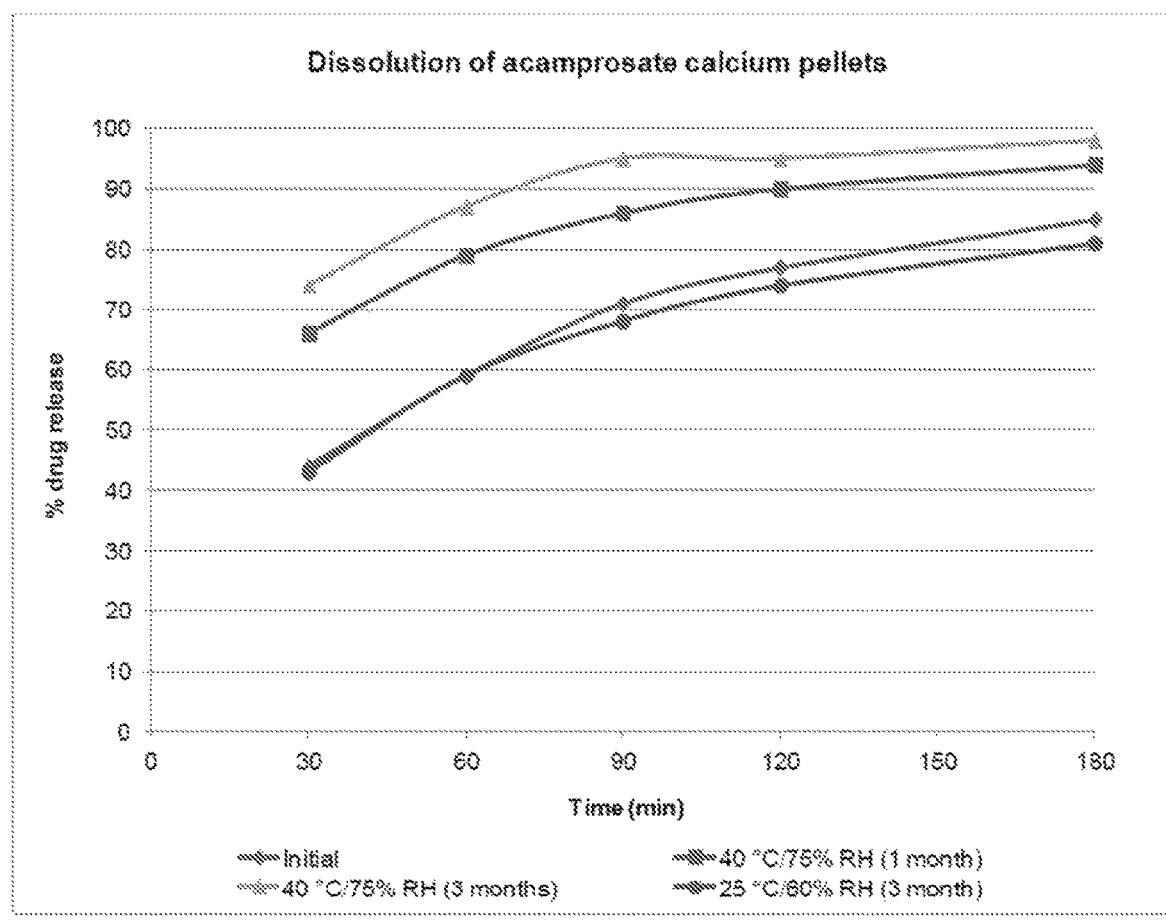

FIGURE 2: Dissolution profile of open petri plate study for sprinkles with 5% ethyl cellulose + 40% enteric coating
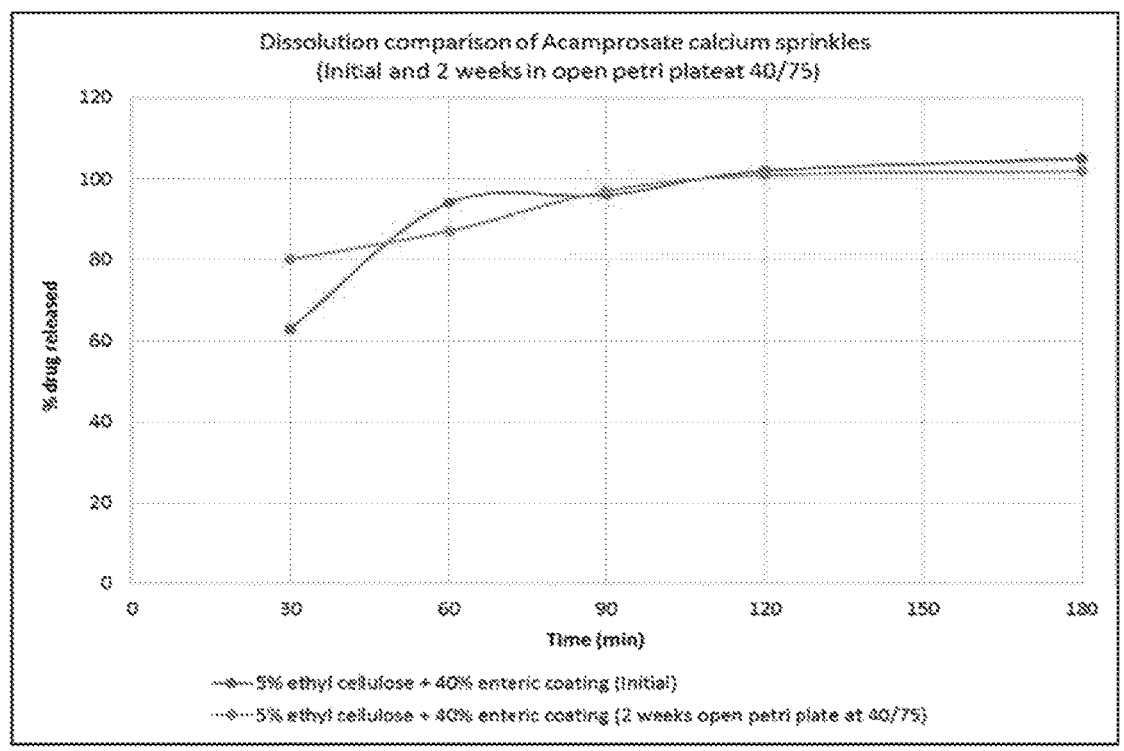

FIGURE 3: Dissolution profile of open petri plate study for sprinkles with 10% ethyl cellulose + 40% enteric coating
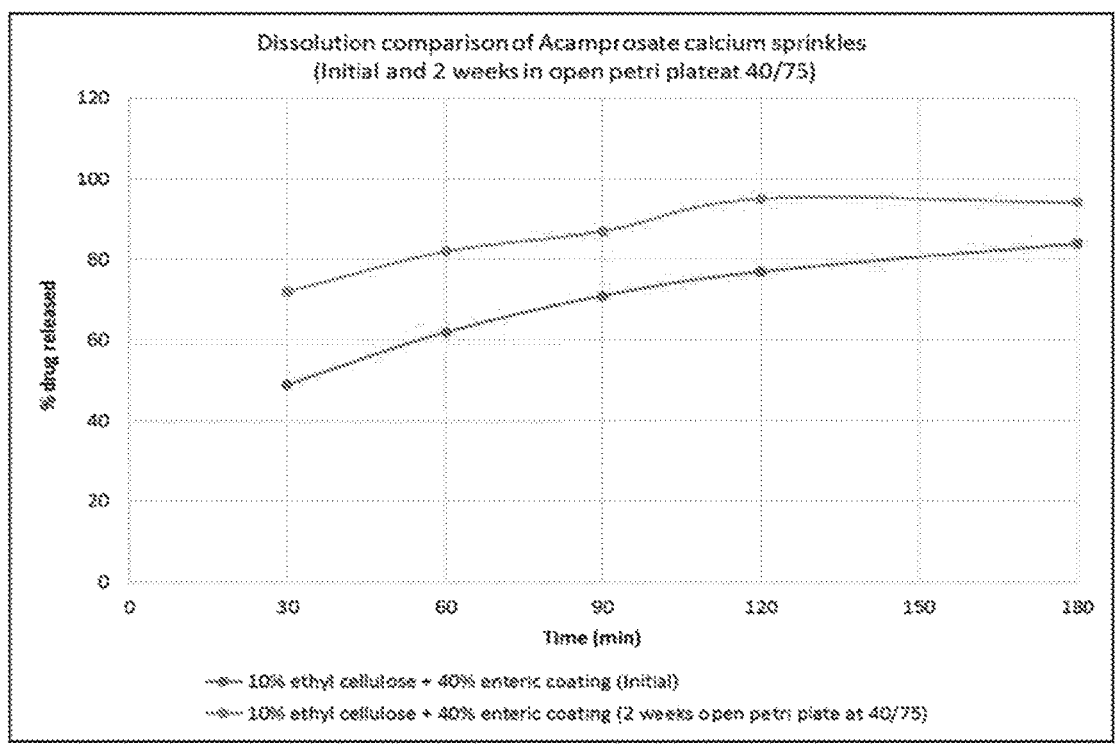

FIGURE 4: Dissolution profile of open petri plate study for sprinkles with 10% ethyl cellulose + 30% enteric coating
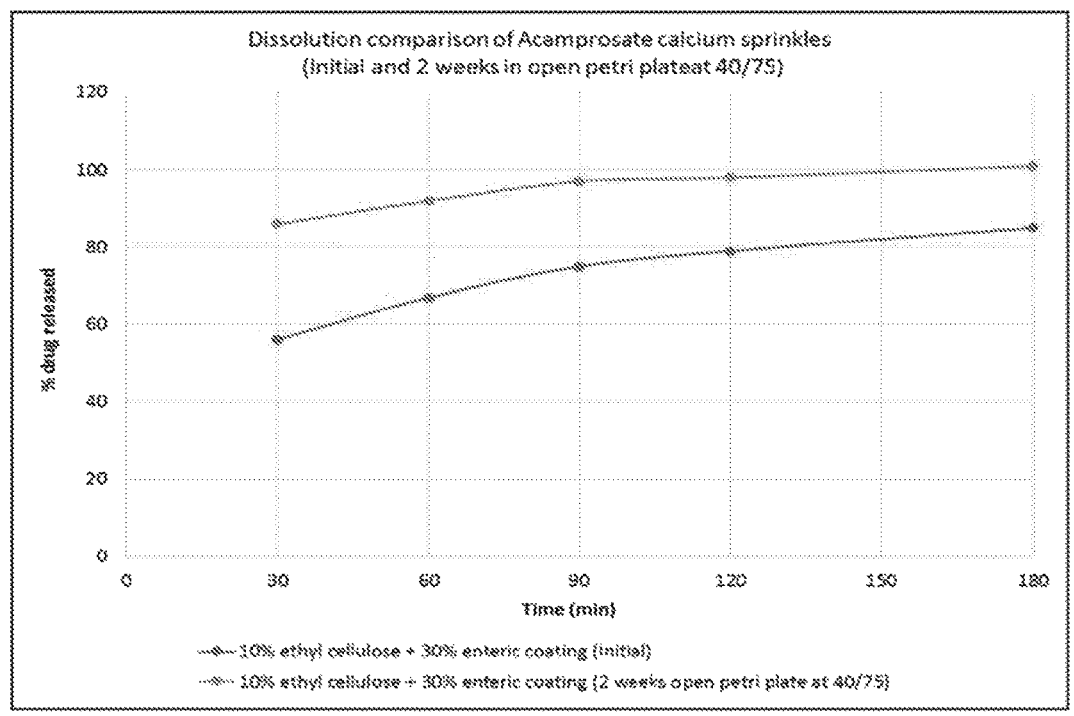

FIGURE 5: Dissolution profile of Acamprosate Calcium Sprinkles (5% ethyl cellulose + 40% eudragit coating)
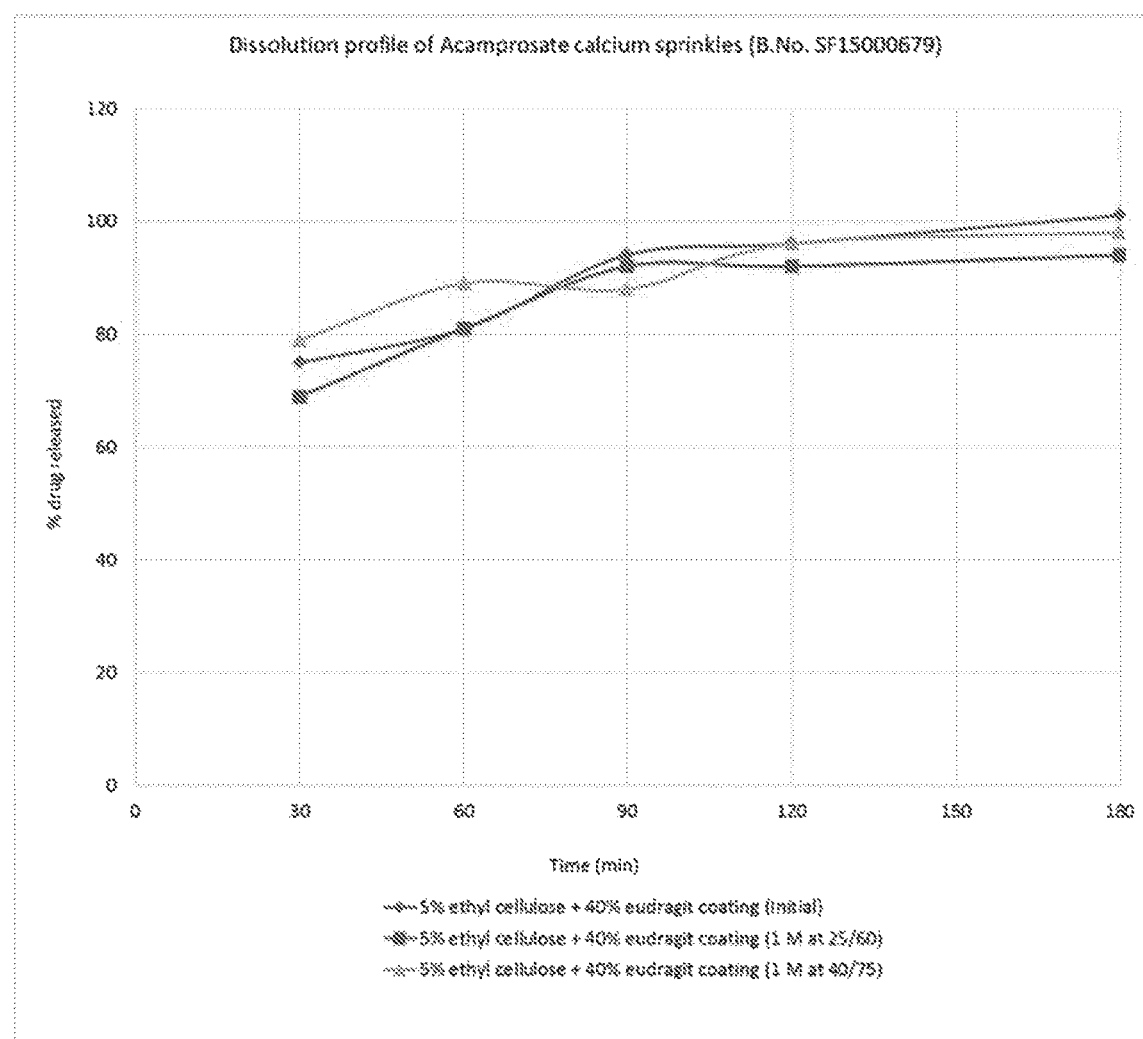

FIGURE 6: Dissolution profile of Acamprosate Calcium Sprinkles (5% ethyl cellulose + 40% eudragit coating)
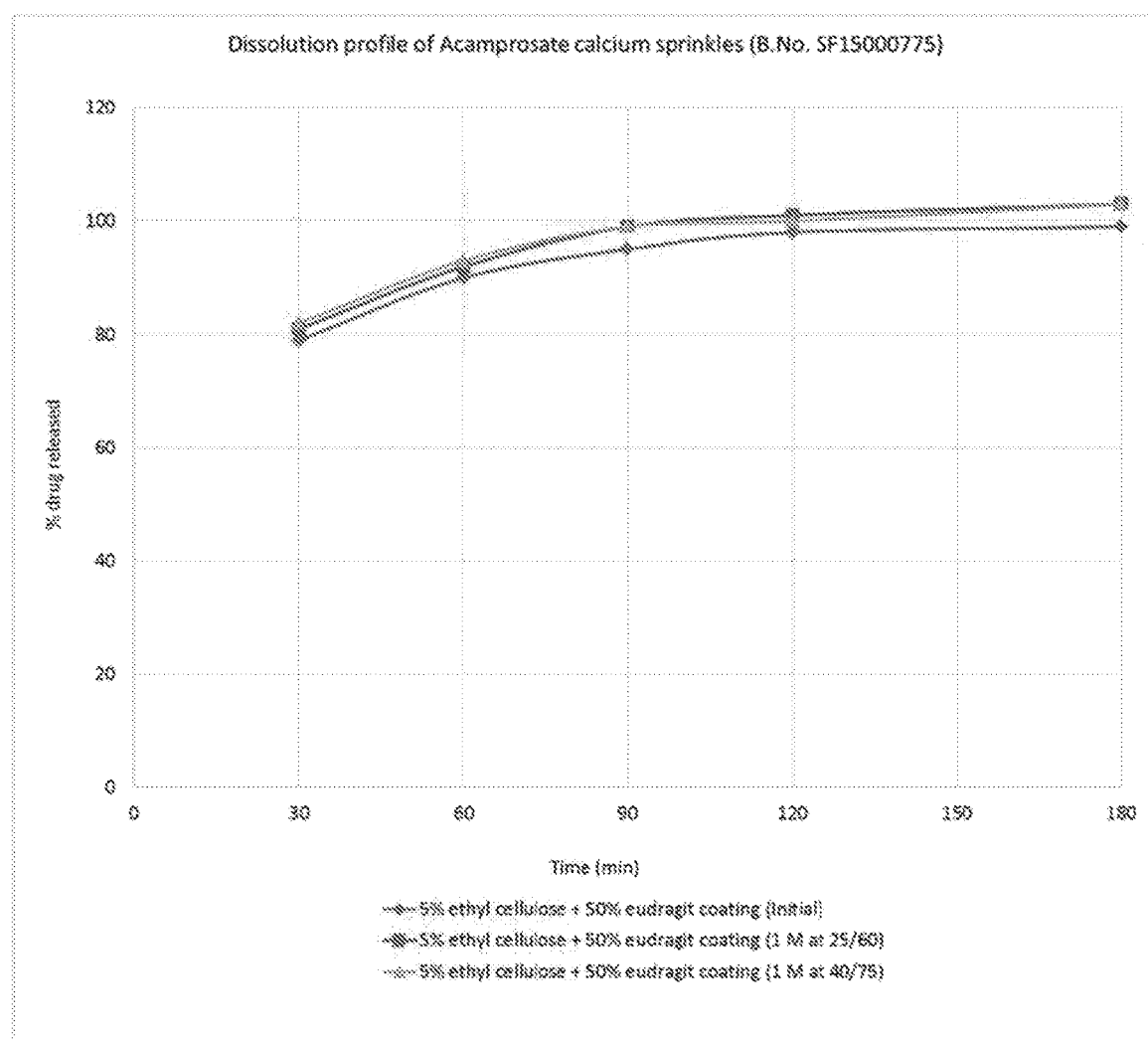

FIGURE 7: Day 1 PK during the first 12 hour period
|  | Cmax (ng) | $AUC_{0-12}$ (ng*hr/ml) | Tmax (hours) |
|---|---|---|---|
| Sprinkle | 4280 | 25,300 | 4.7 |
| EC | 4640 | 27,500 | 3.0 |
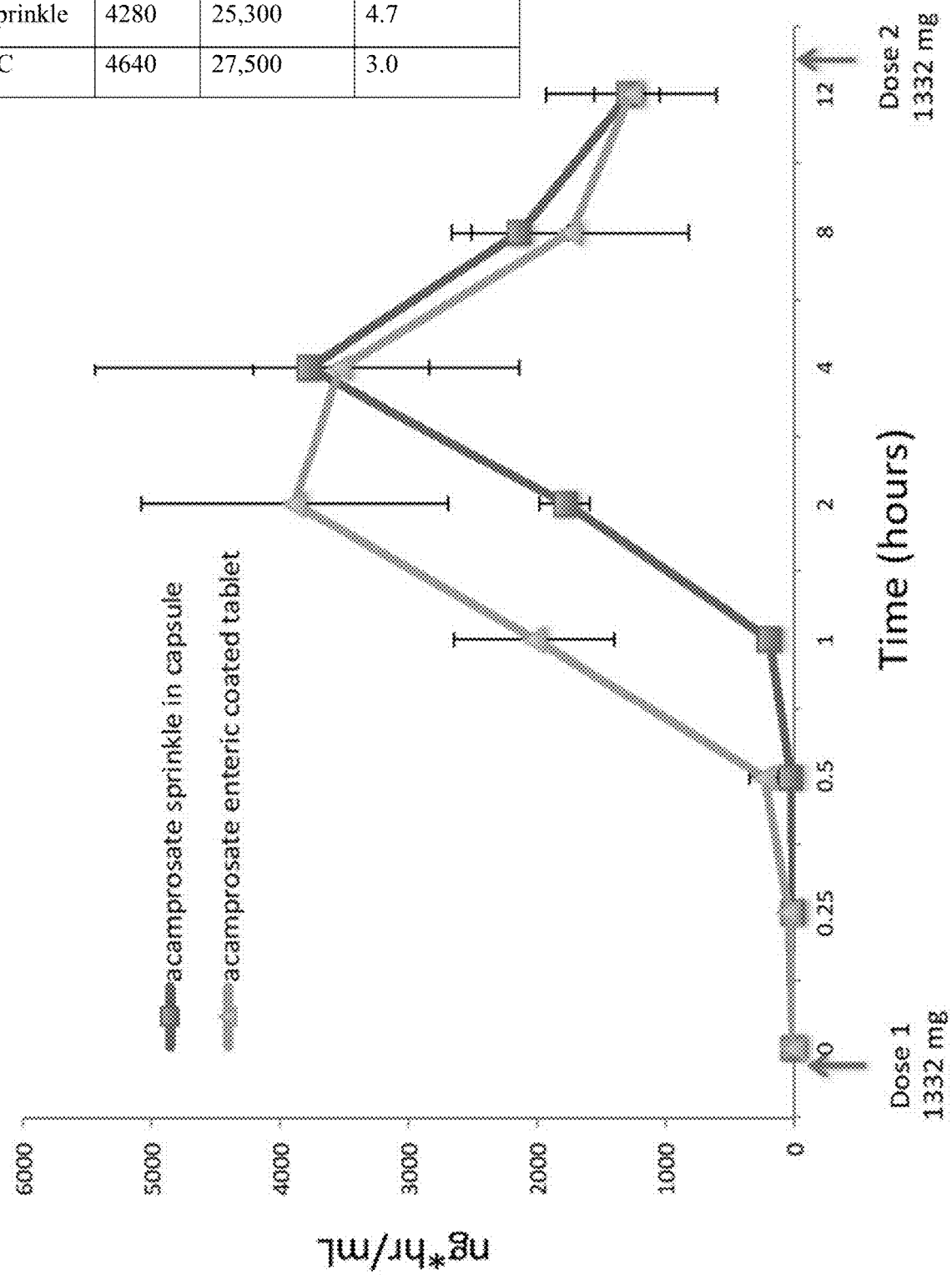

FIGURE 8: Day 1 PK for the 666 mg BID study
|  | Cmax (ng) | $AUC_{0-12}$ (ng*hr/ml) | $AUC_{0-24}$ (ng*hr/ml) | Tmax (hours) |
|---|---|---|---|---|
| Sprinkle | 2400 | 6770 | 18,800 | 13.5 |
| EC | 3620 | 20,800 | 26,200 | 4.7 |
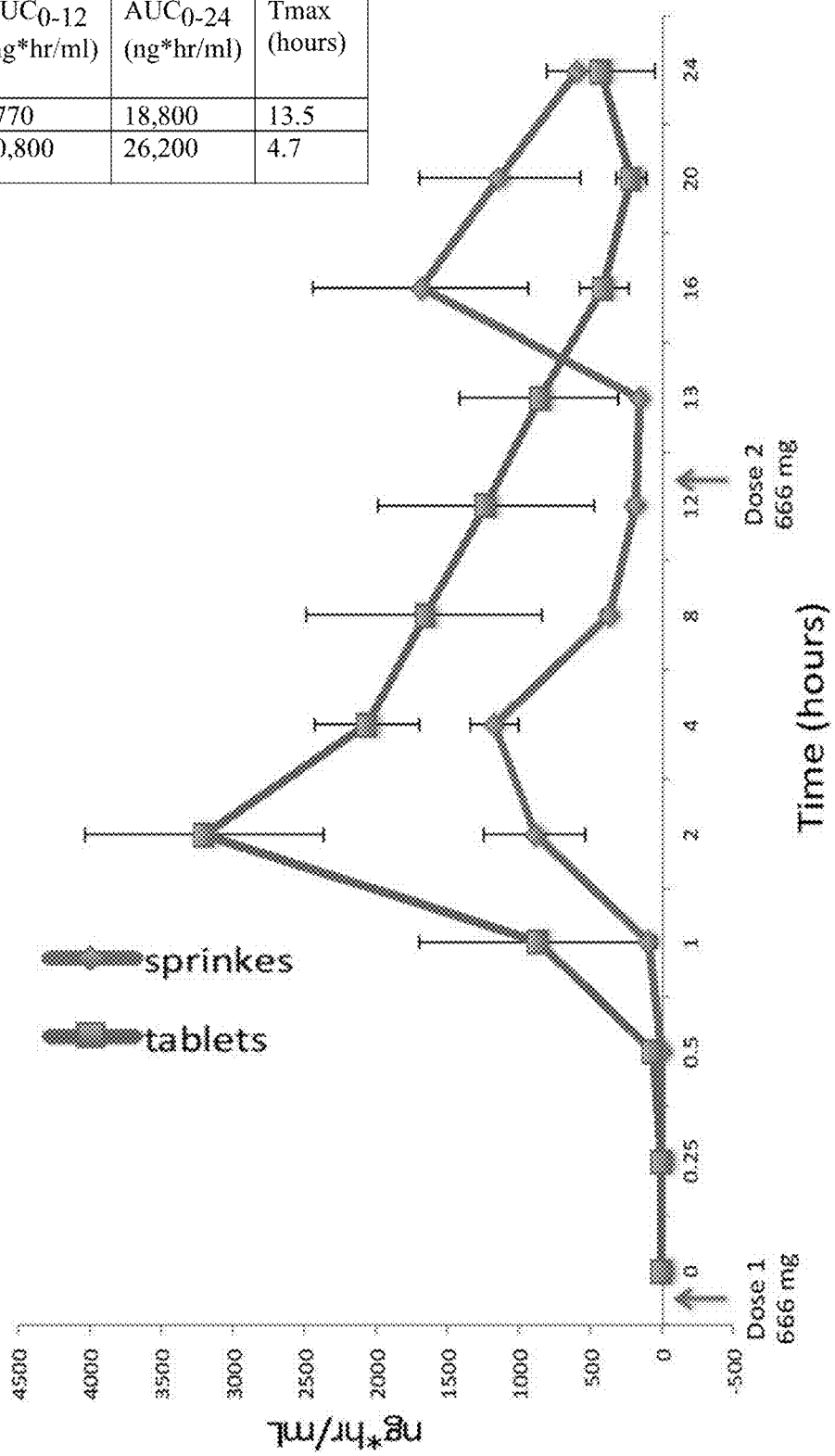

FIGURE 9: PK- 1332 mg (666 mg BID) Day 1--Campral vs. SF679 vs. SF775 (left) compared to Campral vs. SF999 (right)
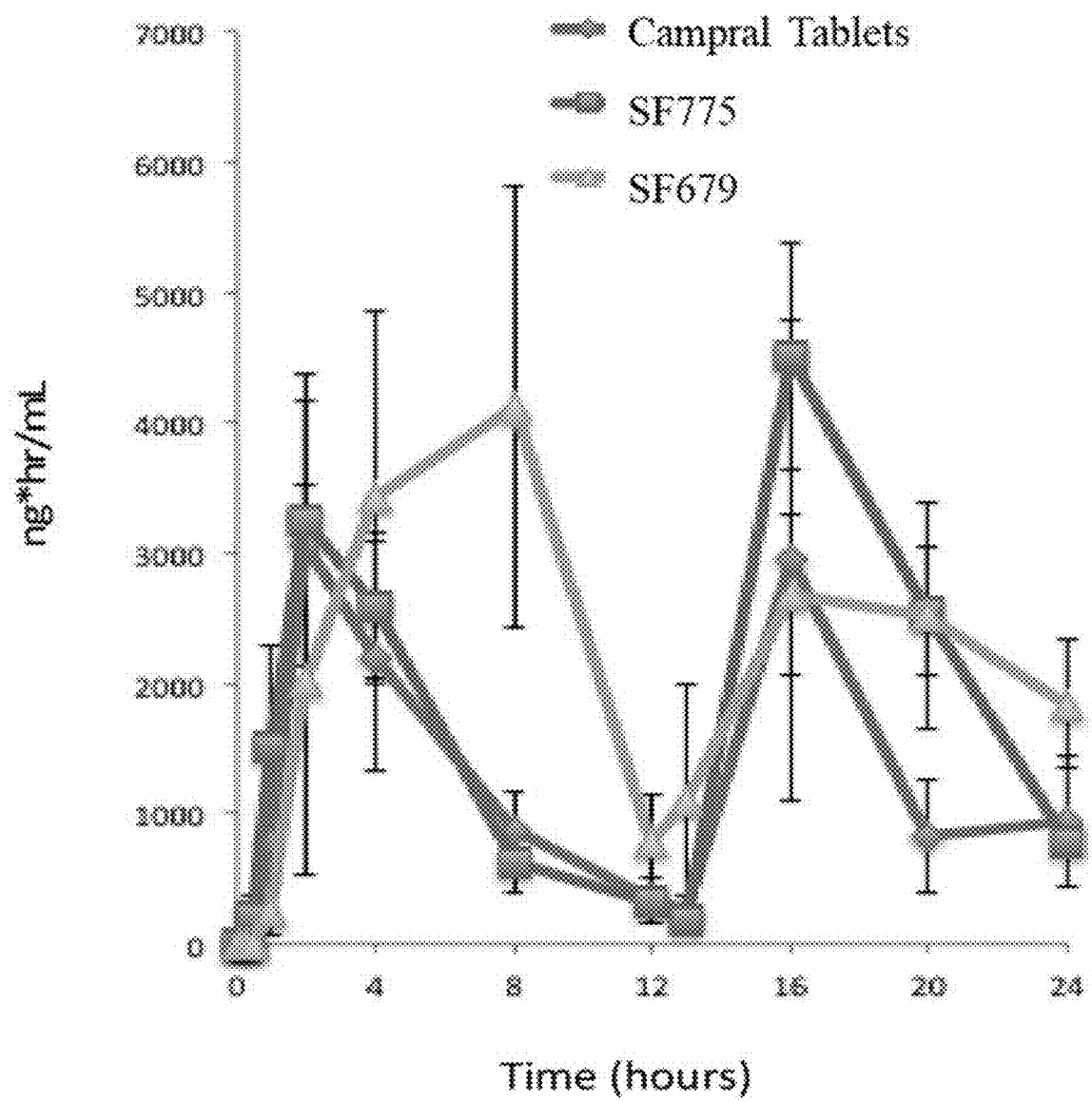

FIGURE 10: PK- 1332 mg (666 mg BID) Day 1 vs. Day 4--Campral vs. SF679 vs. SF775
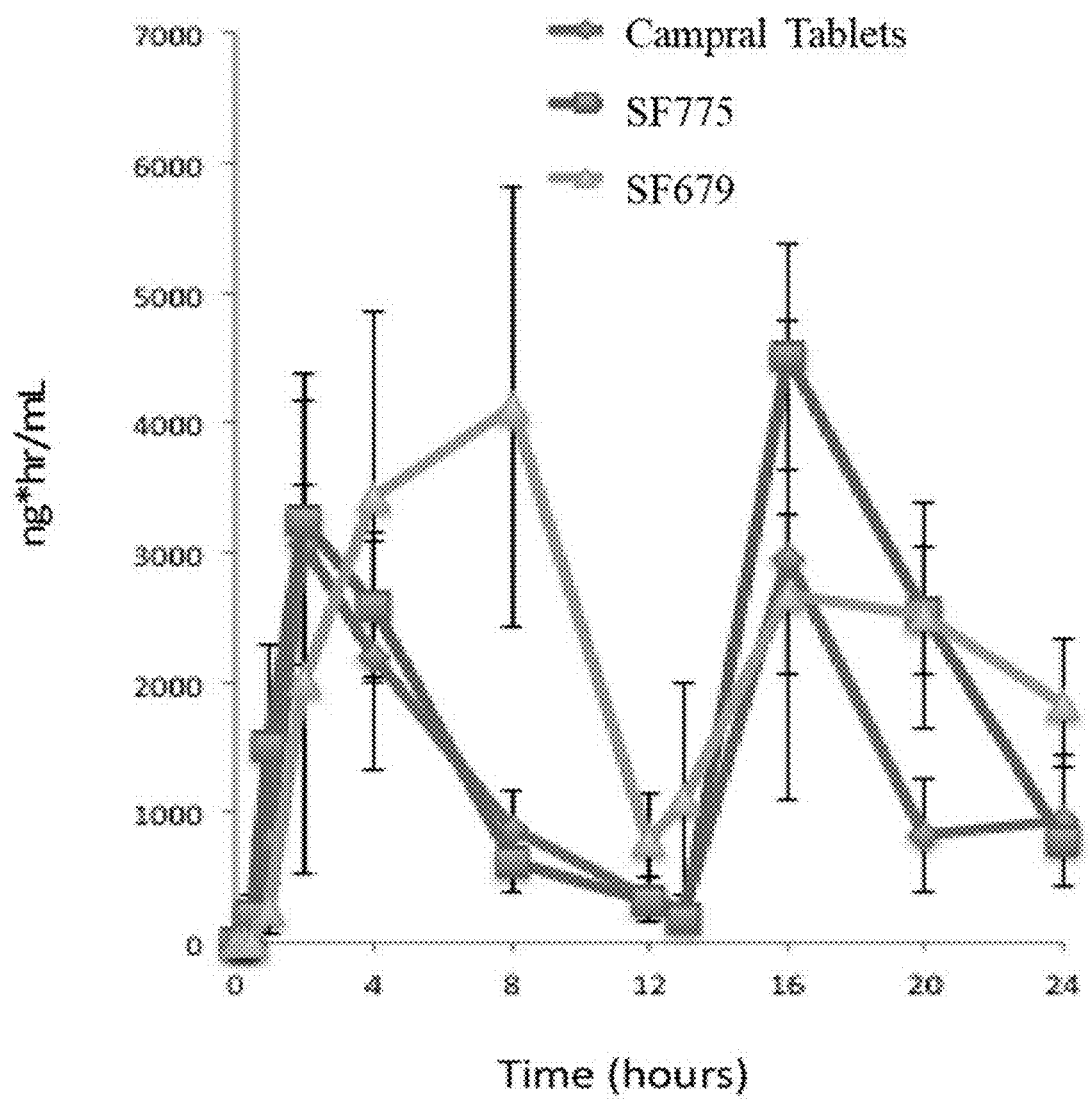

SPRINKLE FORMULATIONS OF ACAMPROSATE

CROSS-REFERENCE TO RELATED APPLICATION

This application is a U.S. national application under 37 C.F.R. § 371(b) of International Application Serial No. PCT/US2016/030725 filed May 4, 2016, which claims priority under 35 U.S.C. § 119(e) to U.S. Provisional Application No. 62/260,161, filed on Nov. 25, 2015, and U.S. Provisional Application No. 62/156,842, filed on May 4, 2015, the entire disclosures of which are incorporated herein by reference.

FIELD OF THE INVENTION

The present invention relates to sprinkle formulations of acamprosate pellets and their use as a medicament.

BACKGROUND 3-(Acetylamino)propylsulfonic acid, also referred to as N-acetylhomotaurine or acamprosate:

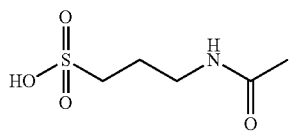

is a derivative of homotaurine, a naturally occurring structural analog of γ-aminobutyric acid (GABA) that appears to affect multiple receptors in the central nervous system (CNS). As an antiglutamatergic agent, acamprosate is believed to exert a neuropharmacological effect as an antagonist of N-methyl-D-aspartate (NMDA) receptors. The mechanism of action is believed to include blocking of the $Ca^{2+}$ channel to slow $Ca^{2+}$ influx and reduce the expression of c-fos, leading to changes in messenger RNA transcription and the concomitant modification to the subunit composition of NMDA receptors in selected brain regions (Zornoza et al., *CNS Drug Reviews*, 2003, 9(4), 359-374; and Rammes et al., *Neuropharmacology* 2001, 40, 749-760). There is also evidence that acamprosate may interact with excitatory glutamatergic neurotransmission in general, and as an antagonist of the metabotropic glutamate receptor subtype 5 (mGluR5) in particular (De Witte et al., *CNS Drugs* 2005, 19(6), 517-37). The glutamatergic mechanism of action of acamprosate may explain the effects of acamprosate on alcohol dependence, and suggests other therapeutic activities, such as in neuroprotection.

A number of issued patents and published patent applications relate to the use of acamprosate as a medicament. For example, U.S. Pat. Nos. 6,391,922 and 6,689,816 disclose a novel treatment for neuropsychiatric disorders, including anxiety disorders, mood disorders, psychotic disorders, somatoform disorders, and neuropsychiatric symptoms resulting from movement disorders. The treatment utilizes any agent that simultaneously act as NMDA-type glutamate receptor antagonists and GABA-A receptor agonists. Preferably, these two activities are characteristic of a single agent, for example, acamprosate (calcium N-acetylhomotaurinate). Alternatively, separate agents having these activities can be combined as a compound or mixture and thereby administered together. The invention also provides for a third agent that acts as a non-competitive NMDA-receptor blocking agent or ion channel blocker that augments the effect of the primary treatment. A particularly preferred ion channel blocking agent is magnesium.

U.S. Pat. No. 7,745,493 discloses a novel treatment for movement disorders, including tardive dyskinesia, tic disorders, Tourette's syndrome, and blepharospasm, and other focal dystonias. The treatment utilizes agents that simultaneously act as NMDA-type glutamate receptor antagonists and GABA-A receptor agonists. Preferably, these two activities are characteristic of a single agent, for example acamprosate. Alternatively, separate agents having these activities can be combined and administered together. The invention also provides a third agent that acts as a non-competitive NMDA-receptor blocking agent or ion channel blocker that augments the effect of the primary treatment. A particularly preferred ion channel blocking agent is magnesium. Alternatively, magnesium can be administered alone for prevention and treatment of movement disorders.

U.S. Pat. No. 8,865,769 discloses combinations and methods for the treatment of neurological disorders related to glutamate excitotoxicity and Amyloid 3 toxicity. More specifically, the invention relates to novel combinatorial therapies of Multiple Sclerosis, Alzheimer's disease, Alzheimer's disease related disorder, Amyotrophic Lateral Sclerosis, Parkinson's disease, Huntington's disease, neuropathic pain, alcoholic neuropathy, alcoholism or alcohol withdrawal, or spinal cord injury, based on Baclofen and Acamprosate combination.

Published US Patent application no. 2011/0294879 discloses methods of treating fragile X syndrome, fragile X-associated tremor/ataxia syndrome, Down's syndrome and/or, comprising administering a prodrug of acamprosate to a subject suffering therefrom.

WO 2010093859 A1 relates to subjects who were diagnosed with either comorbid or idiopathic autism and fragile x syndrome and treated with acamprosate. Patients generally showed marked improvements in primary outcomes as assessed using, for example, standard clinic measures for functionality including the Clinical Global Impressions Improvement (CGI-I) and the Clinical Global Impressions Severity (CGI-S) scales.

A number of issued patents and published patent applications relate to forms and formulations of acamprosate. For example, U.S. Pat. No. 6,426,087 discloses an orally administrable galenic form allowing improved absorption by the transmembrane or paracellular route in the gastrointestinal tract of active ingredients which are hydrophilic or ionizable in physiol. media, comprising at least one such active ingredient, an absorption-promoting agent having an HLB>8, the absorption-promoting agent consisting of one or more lipid substances chosen from: polysorbates; polyoxyethylene ethers; esters of polyoxyethylene and fatty acids; fatty acids; fatty alcs.; bile acids and their salts with pharmaceutically acceptable cations; esters of C1-C6 alkanol with fatty acids; esters of polyol with fatty acids, the polyol comprising from 2 to 6 hydroxyl functional groups; and polyglycolyzed glycerides; in combination with one or more pharmaceutically acceptable excipients, the pharmaceutical forms comprising captopril being excluded. A controlled-release tablet contained (1) cores contg. calcium acamprosate 50, Gelucire 44/14 10, Compritol 10, microcryst. cellulose 19, Povidone 10, and Mg stearate 1% and (2) a film-coating compn. contg. HPMC 64, PEG-4000 15, and talc 21%.

U.S. Pat. No. 6,512,009 discloses a pharmaceutical composition for the treatment of alcohol and drug dependence, comprising a therapeutically effective amount of a combination of: (i) an opioid antagonist; and (ii) a NMDA receptor complex modulator. A pharmaceutical kit is also provided, comprising these two substances. The opioid antagonist can, for example, be naltrexone and the NMDA receptor complex modulator can be a spermidine site modulator such as acamprosate.

U.S. Pat. No. 7,994,218 discloses pantoic acid ester neopentyl sulfonyl ester prodrugs of acamprosate, pharmaceutical compositions comprising such prodrugs, and methods of using such prodrugs and compositions thereof for treating diseases. In particular, acamprosate prodrugs exhibiting enhanced oral bioavailability and methods of using acamprosate prodrugs to treat neurodegenerative disorders, psychotic disorders, mood disorders, anxiety disorders, somatoform disorders, movement disorders, substance abuse disorders, binge eating disorder, cortical spreading depression related disorders, tinnitus, sleeping disorders, multiple sclerosis, and pain are disclosed.

U.S. Pat. No. 8,268,352 discloses a novel modified release dosage form comprising of a high solubility active ingredient, which utilizes dual retard technique to effectively reduce the quantity of release controlling agents. The dosage form can optionally comprise another active ingredient as an immediate release form or modified release form. The invention also relates to a process for preparing the said formulation.

U.S. Pat. No. 9,000,046 discloses gastric retentive dosage forms for sustained release of acamprosate which may allow once- or twice-daily dosing for both acute and long-term treatment of a disorder including alcohol dependence, tinnitus, sleep apnea, Parkinson's disease, levodopa-induced dyskinesias in Parkinson's disease, Alzheimer's disease, Huntington's disease, Amyotrophic lateral sclerosis, Cortical spreading depression, migraine, schizophrenia, anxiety, tardive dyskinesia, spasticity, multiple sclerosis, various types pain, or binge eating. Methods of treatment using the dosage forms and methods of making the dosage forms are also described.

Published US Patent application no. 2011/0182953 discloses a new polymorphic form of calcium acetyl-homotaurinate, designated as form B, and processes for the preparation of said form B and of the known crystalline form.

Published US patent application no. 2013/0310456 discloses embodiments generally related to acamprosate formulations, methods of use of the formulations, methods of using the formulations in combination with at least one other medication, and combination products and compositions comprising the formulations and at least one other medication, such as neuroleptic (antipsychotic) and/or antidepressant drugs.

Acamprosate is a polar molecule that lacks the requisite physicochemical characteristics for effective passive permeability across cellular membranes. As a consequence, the oral bioavailability of acamprosate in humans is only about 11%, and poor absorption of the drug from the GI tract likely contributes to its limited tolerability. One consequence is that a relatively large tablet has been required to achieve a therapeutic effect.

Acamprosate calcium, marketed as Campral® by Forest Pharma, was first approved by the FDA in 2004. Campral® is indicated for the maintenance of abstinence from alcohol in patients with alcohol dependence who are abstinent at treatment initiation. Campral® is supplied as an enteric-coated tablet for oral administration. Each Campral® tablet contains acamprosate calcium 333 mg, equivalent to 300 mg of acamprosate. Inactive ingredients in Campral® tablets include: crospovidone, microcrystalline cellulose, magnesium silicate, sodium starch glycolate, colloidal anhydrous silica, magnesium stearate, talc, propylene glycol and Eudragit® L 30 D or equivalent. Sulfites were used in the synthesis of the drug substance and traces of residual sulfites may be present in the drug product. Campral® 333 mg tablets are enteric-coated, white, round, biconvex tablets, identified with "333" debossed on one side. The recommended dose of Campral® is two 333 mg tablets (each dose should total 666 mg) taken three times daily. A lower dose may be effective in some patients. Although dosing may be done without regard to meals, dosing with meals was employed during clinical trials and is suggested in those patients who regularly eat three meals daily. As an enteric-coated tablet, any disruption of the coating allows for immediate dissolution of the tablet before moving through the upper digestive tract and into the lower digestive tract for absorption. When the pill's enteric-coating is broken (i.e. chewed or cut), then an adverse reaction is encouraged and GI distress (diarrhea nausea and vomiting) increases.

The current formulation of Campral® is a solid formed, 333 mg round tablet and is a 10 mm in size. Also known as AOTAL in Europe, the drug is available in 400 mg and 800 mg tablets. The size of the tablet presents a challenge for both pediatric and adult patients. The FDA issued draft guidance on size, shape and other physical attributes of generic tablets and capsules which outlines the difficulties swallowing tablets and capsules for many individuals and can lead to a variety of adverse events and patient noncompliance with treatment regimens. (www.fda.gov/downloads/drugs/guidancecomplianceregulatory information/guidances/ucm377938.pdf) The guidance estimates over 16 million people in the U.S. have some difficulty swallowing a tablet or capsule. The size and shape of the tablets can affect the transit of the product through the pharynx and esophagus and may directly affect the patient's ability to swallow a product. This can lead to disintegration of the product in the esophagus and the potential for ulceration, stricture or perforation as well as other adverse events like pain, gagging, choking and aspiration. The studies presented by the FDA suggest that tablets larger than 8 mm in diameter are associated with increases in patient complaints and difficulties and increased esophageal transit time.

Consistent with its activity as a functional glutamateric antagonist, a clinical study of Campral® (acamprosate calcium) in subjects with Fragile X Syndrome (FXS) and comorbid autistic disorder demonstrated significant symptomatic improvements as assessed by the investigators' Clinical Global Impression (CGI-I), with improvements in communication and social interaction skills being particularly noteworthy (Erickson et al, J. Autism Dev. Disord. 2010). Gastrointestinal distress (nausea and vomiting) are commonly observed side effects in subjects receiving acamprosate, and adverse GI events were observed in the majority of Fragile X subjects treated in this study.

A published study conducted by Bailey (Bailey D. B., et. al. Medication Utilization for Targeted Symptoms in Children and Adults with Fragile X Syndrome: US Survey. J Dev Behav Pediatr. 2012 33:62-69) further demonstrated that between 40%-90% of pediatric patients with Fragile X Syndrome (n=1,361 FXS patients) had significant difficulty swallowing a whole solid pill. While pill swallowing remains a difficult exercise for a majority pediatric patients, it does improve with age and training. However, this challenge still remains for at least 20% of Fragile X Syndrome adults, elderly patients or populations with swallowing difficulties. This data is consistent with the clinical experience by Dr. Erickson and has been a barrier to recruiting patients for open-label pilot studies with Campral®.

There is still a long-felt and unmet need for new oral formulations of acamprosate which do not induce gastrointestinal problems to treat patients who are unable or unlikely to swallow tablet or capsule formulations of the drug.

BRIEF DESCRIPTION OF THE DRAWINGS

FIG. 1 shows a dissolution profile of acamprosate calcium enteric-coated sprinkles (#25/30).

FIG. 2 shows a dissolution profile of open petri plate study for sprinkles with 5% ethyl cellulose+40% enteric coating.

FIG. 3 shows a Dissolution profile of open petri plate study for sprinkles with 10% ethyl cellulose+40% enteric coating.

FIG. 4 shows a Dissolution profile of open petri plate study for sprinkles with 10% ethyl cellulose+30% enteric coating.

FIG. 5 shows a dissolution profile of Acamprosate Calcium Sprinkles (5% ethyl cellulose+40% eudragit coating).

FIG. 6 shows a dissolution profile of Acamprosate Calcium Sprinkles (5% ethyl cellulose+50% eudragit coating).

FIG. 7 shows day 1 PK during the first 12 hour period.

FIG. 8 shows the day 1 PK for the 666 mg BID study.

SUMMARY OF THE INVENTION

Figure 9:
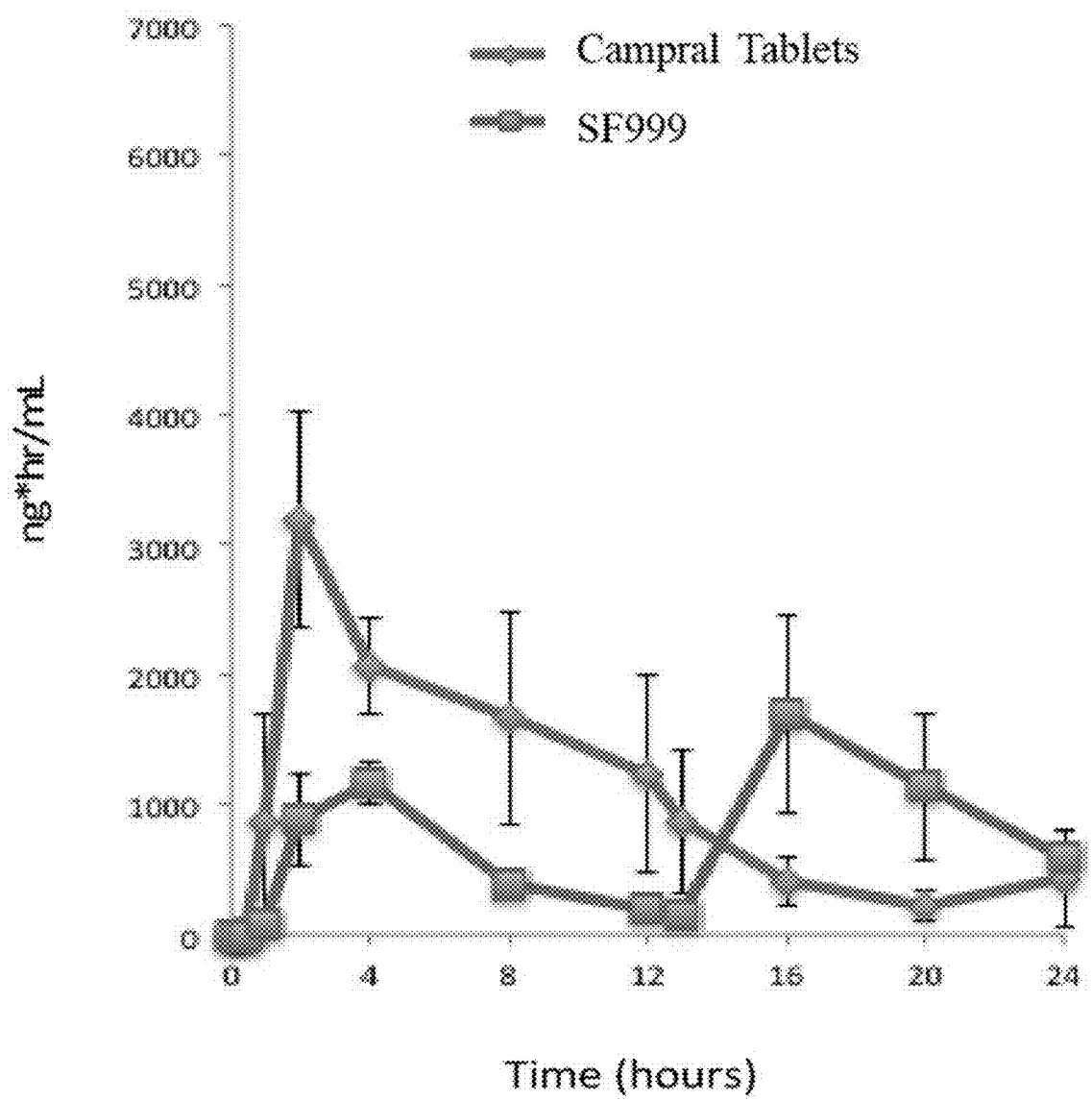
FIG. 9 shows PK-1332 mg (666 mg BID) Day 1—Campral vs. SF15000679 vs. SF15000775 (left) compared to Campral vs. SF14000999 (right).

In a $1^{st}$ aspect, the present invention provides an orally-administrable, pharmaceutical formulation comprising: a plurality of sprinkles, wherein:
the sprinkles comprise a core, a sustained release coating, and an enteric coating; and
the core comprises an active ingredient and a diluent.

In a 1st embodiment, the active ingredient is a homotaurine analog selected from the group consisting of: an acetylaminopropane sulfonate, an acetylaminopropane sulfonate salt, taltrimide, and tauromustine.

In a preferred embodiment, the active ingredient is 3-acetamidopropane-1-sulfonic acid or a pharmaceutically acceptable salt thereof.

In a preferred embodiment, the active ingredient is acamprosate calcium.

In a $2^{nd}$ embodiment, the diluent comprises Microcrystalline Cellulose (MCC) or a cellulose gel.

In a preferred embodiment, the diluent consists essentially of Microcrystalline Cellulose (MCC).

In a preferred embodiment, the diluent comprises Avicel PH101.

In a preferred embodiment, the diluent consists essentially of Avicel PH101.

In a $3^{rd}$ embodiment, the sustained release coating comprises a thermoplastic cellulose ether.

In a preferred embodiment, the sustained release coating comprises ethyl cellulose.

In a preferred embodiment, the sustained release coating comprises Ethyl cellulose 20 standard.

In a preferred embodiment, the sustained release coating further comprises triethyl citrate.

In a preferred embodiment, the ratio of Ethyl cellulose 20 standard:triethyl citrate is about 5 to about 30 w/w %.

In a preferred embodiment, the ratio of Ethyl cellulose 20 standard:triethyl citrate is about 25 w/w %.

In a $4^{th}$ embodiment, the enteric coating comprises an anionic copolymer based on methacrylic acid and ethyl acrylate.

In a preferred embodiment, the enteric coating comprises a Eudragit.

In a preferred embodiment, the enteric coating comprises a Eudragit S.

In a preferred embodiment, the enteric coating comprises a Eudragit L.

In a preferred embodiment, the enteric coating comprises Eudragit L100 55.

In a preferred embodiment, the enteric coating further comprises triethyl citrate.

In a preferred embodiment, the enteric coating further comprises talc.

In a preferred embodiment, the enteric coating further comprises triethyl citrate and talc.

In a preferred embodiment, the ratio of Eudragit L100 55:triethyl citrate:talc is about 100 to about 25 to about 50 w/w %.

In a preferred embodiment, the ratio of Eudragit L100 55:triethyl citrate:talc is about 100 to about 25 to about 50 w/w %.

In a $5^{th}$ embodiment, the plurality of pellets range in size from about 0.5 mm to about 3.1 mm, as determined for a maximum Bead Size for Drug Products Labeled for Sprinkle (per the current US-FDA Guidance at http://www.fda.gov/downloads/drugs/guidancecomplianceregulatory information/guidances/ucm240243.pdf)

In a $6^{th}$ embodiment, the plurality of pellets range in size from about 0.6 mm to about 1.5 mm, as measured using an ASTM Mesh.

In a $7^{th}$ embodiment, the active ingredient is homogeneously dispersed in the pellets.

In an $8^{th}$ embodiment, the surface of the core is substantially smooth in texture.

In a $9^{th}$ embodiment, the surface of the core is substantially non-porous.

In a $10^{th}$ embodiment, the formulation is a sustained release formulation of acamprosate calcium, characterized by a release profile wherein less than about 90% of the acamprosate calcium is released in 30 minutes pH 6.8.

In a preferred embodiment, less than about 50% of the acamprosate calcium is released in 120 min at pH 1.2.

In an $11^{th}$ embodiment, the formulation is a modified release formulation of acamprosate calcium, characterized by a release profile wherein greater than about 10% of the acamprosate calcium is released in 30 min at pH 1.2.

In a preferred embodiment, greater than about 10% of the acamprosate calcium is released in 120 min at pH 1.2.

In a $12^{th}$ embodiment, the active ingredient comprises about 5 to about 75 w/w % (active ingredient: diluent) of the core.

In a preferred, the active ingredient comprises about 5 to about 65 w/w % (active ingredient: diluent) of the core.

In a preferred embodiment, the active ingredient comprises about 5 to about 60 w/w % (active ingredient: diluent) of the core.

In a preferred embodiment, the active ingredient comprises about 45 to about 65 w/w % (active ingredient: diluent) of the core.

In a preferred embodiment, the active ingredient comprises about 50 to about 60 w/w % (active ingredient: diluent) of the core.

In a preferred embodiment, the active ingredient comprises about 10 to about 40 w/w % (active ingredient: diluent) of the core.

In a preferred embodiment, the active ingredient comprises about 20 to about 35 w/w % (active ingredient: diluent) of the core.

In a preferred embodiment, the active ingredient comprises about 50 w/w % (active ingredient: diluent) of the core.

In a preferred embodiment, the active ingredient comprises about 60 w/w % (active ingredient: diluent) of the core.

In a 13th embodiment, the plurality of pellets is contained in a capsule.

In a preferred embodiment, the capsule contains a unit dose of the active ingredient.

In a 14th embodiment, the plurality of pellets is contained in a sachet.

In a preferred embodiment, the sachet contains a unit dose of the active ingredient.

In a preferred embodiment, the active ingredient is acamprosate calcium and the unit dose is about 100 mg to about 2500 mg.

In a preferred embodiment, the unit dose is about 333 mg.

In a 15th embodiment, the sustained release coating is about 1 to about 30 w/w % (sustained release coating: core).

In a preferred embodiment, the sustained release coating is about 1 to about 10 w/w % (sustained release coating: core).

In a preferred embodiment, the sustained release coating is about 3 to about 7 w/w % (sustained release coating: core).

In a preferred embodiment, the sustained release coating is about 5 w/w % (sustained release coating: core).

In a 16th embodiment, the enteric coating is about 25 to about 60 w/w % (enteric coating: core).

In a preferred embodiment, the enteric coating is about 35 to about 55 w/w % (enteric coating: core).

In a preferred embodiment, the enteric coating is about 40 to about 50 w/w % (enteric coating: core).

In a preferred embodiment, the enteric coating is about 50 w/w % (enteric coating: core).

In a preferred embodiment, the enteric coating is about 40 w/w % (enteric coating: core).

In a 17th embodiment, the enteric coating is about 25 to about 60 w/w % (enteric coating: core+sustained release coating).

In a preferred embodiment, the enteric coating is about 35 to about 55 w/w % (enteric coating: core+sustained release coating).

In a preferred embodiment, the enteric coating is about 40 to about 50 w/w % (enteric coating: core+sustained release coating).

In a preferred embodiment, the enteric coating is about 50 w/w % (enteric coating: core+sustained release coating).

In a preferred embodiment, the enteric coating is about 40 w/w % (enteric coating: core+sustained release coating).

In an 18th embodiment, the pharmaceutical formulation further comprises one or more additives selected from the group consisting of: a lubricant, colorant, flow agent, glidant, filler, perfume, flavor, flavor enhancer, or effervescent agent.

In a 19th embodiment, the pharmaceutical formulation further comprises a mGluR antagonist.

In a 20th embodiment, the pharmaceutical formulation further comprises an antipsychotic agent.

In a 21st embodiment, the pharmaceutical formulation further comprises includes a antipsychotic (neuroleptic) medication, a selective serotonin reuptake inhibitor (SSRI), a serotonin-norepinephrine reuptake inhibitor (SNRI), an antidepressant, or an anti-anxiety agent.

In a 22nd embodiment, the pharmaceutical formulation further comprises the $GABA_A$ agonist bamaluzole, D-Cycloserine, GABA, gabamide, GABOB, gaboxadol, ibotenic acid, isoinpecotic acid, muscimol, phenibut, picamilon, progabide, SL75102, Thiomuscimol, or a positive allosteric modulator that increases the activity of $GABA_A$, such as alcohols, alprazolam, barbiturates, benzodiazepines and nonbenzodiazepines.

In a 23rd embodiment, the pharmaceutical formulation further comprises a $GABA_B$ receptor agonist, a muscarinic receptor antagonist, a stimulant, a nicotinic receptor agonist, an endocannabinoid receptor antagonist, an AMPA agonist, an antidepressant, an a2-adrenergic agonist, or an anticonvulsant.

In a 2nd aspect, the present invention provides a method of treating a medical condition in a patient comprising: administering to a patient in need thereof an effective amount of an orally-administrable, pharmaceutical formulation of the present invention.

In a 1st embodiment, the medical condition is age-related cognitive impairment, Mild Cognitive Impairment (MCI), dementia, Alzheimer's Disease (AD), prodromal AD, post-traumatic stress disorder (PTSD), schizophrenia, bipolar disorder, amyotrophic lateral sclerosis (ALS), cancer-therapy-related cognitive impairment, drug induced or toxin induced cognitive impairment, mental retardation, Parkinson's disease (PD), autism, compulsive behavior, or substance addiction.

In a 2nd embodiment, the medical condition is Alcohol dependence, tinnitus, sleep apnea, Parkinson's disease, levodopa-induced dyskinesias in Parkinson's disease, Alzheimer's disease, Huntington's disease, Amyotrophic lateral sclerosis, Cortical spreading depression, migraine, schizophrenia, Anxiety, tardive dyskinesia, spasticity, multiple sclerosis, various types of pain, or binge eating.

In a 3rd embodiment, the medical condition is an Autism Spectrum Disorder, Pervasive Development Disorder—Not Otherwise Specified, Idiopathic Autism, Fragile X Syndrome, Asperger's Syndrome, Rhett's Syndrome, or Childhood disintegrative disorder as further referenced in Diagnostic and Statistical Manual of Mental Disorders IV.

In a preferred embodiment, the medical condition is Fragile X Syndrome.

In a 4th embodiment, the medical condition is a neurotransmission or cognitive disorder that is characterized as a glutamate-GABA imbalance; a disorder characterized with disrupted or dysregulated ERK signaling pathway; or a rasopathy resulting in an abnormality in brain development, learning, memory or cognition.

In a 5th embodiment, the administering step comprises: sprinkling the pharmaceutical formulation onto food having about pH<5.5 prior to ingestion.

In a preferred embodiment, the food is applesauce or yogurt.

In a 6th embodiment, a single unit does of the active ingredient is administered 1-4 times per day.

In a preferred embodiment, the single unit dose is administered 2-3 times per day.

It is contemplated, and will be appreciated, that all allowable combinations of the aspects/embodiments described above and elsewhere within this application are contemplated as further aspects/embodiments of the invention.

DETAILED DESCRIPTION

As used herein:

"Bioavailability" refers to the rate and amount of a drug that reaches the systemic circulation of a subject following administration of the drug to the subject and can be determined by evaluating, for example, the plasma or blood concentration-versus-time profile for a drug.

"Enteric coating" refers to a polymer barrier applied to or on an oral medication in order to protect the drug from the lower pH of the stomach and avoiding dissolution and irritation of the stomach.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. When the active ingredient is acamprosate, the preferred salt is the calcium salt.

"Pharmaceutical composition" refers to at least one active ingredient and at least one pharmaceutically acceptable vehicle with which at least one active ingredient is administered to a subject.

"Salt" refers to a chemical compound consisting of an assembly of cations and anions. Salts of a compound of the present disclosure include stoichiometric and non-stoichiometric forms of the salt. In certain embodiments, because of its potential use in medicine, salts of an active ingredient are pharmaceutically acceptable salts.

"Sprinkle formulation" refers to enteric-coated beads or pellets which can be spherical in shape and is currently defined by the FDA to be 0.82 mm to 3.04 mm (+ or −10% variation) in size and can be administered orally with food with or without chewing. Sprinkles can be manufactured in several shapes such as cylindrical, cylindrical with round ends, dumb-bell, ellipsoid or spherical in shape. See "*Guidance for Industry Size of Beads in Drug Products Labeled for Sprinkle*," U.S. Department of Health and Human Services Food and Drug Administration Center for Drug Evaluation and Research (CDER) May 2012 CMC Rev. 1.

"Sachet" is a small flexible package made by bonding, e.g., two layers together on all four sides. In the pharmaceutical arts, the term often refers to single-use, sealed, flexible aluminum pouches which contains a dose of the formulation of which could be presented as a liquid, powder, cream, paste or granule.

"Subject" refers to a mammal, for example, a human.

"Sustained release" refers to release of a compound from a dosage form of a pharmaceutical composition at a rate effective to achieve a therapeutic or prophylactic concentration of the compound, or active metabolite thereof, in the systemic circulation of a subject over a prolonged period of time relative to that achieved by administration of an immediate release formulation of the same compound by the same route of administration. In some embodiments, release of a compound occurs over a time period of at least about 4 hours, at least about 8 hours, at least about 12 hours, at least about 16 hours, at least about 20 hours, and in some embodiments, at least about 24 hours.

"Treating" or "treatment" of any disease refers to arresting or ameliorating a disease or at least one of the clinical symptoms of a disease or disorder, reducing the risk of acquiring a disease or at least one of the clinical symptoms of a disease, reducing the development of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter that may or may not be discernible to the subject. In certain embodiments, "treating" or "treatment" refers to delaying the onset of the disease or at least one or more symptoms thereof in a subject which may be exposed to or predisposed to a disease or disorder even though that subject does not yet experience or display symptoms of the disease.

"Therapeutically effective amount" refers to the amount of a compound that, when administered to a subject for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the subject to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a subject. A therapeutically effective dose may vary from compound to compound, and from subject to subject, and may depend upon factors such as the condition of the subject and the route of delivery. A therapeutically effective dose may be determined in accordance with routine pharmacological procedures known to those skilled in the art.

Reference is now made in detail to certain embodiments of compounds, compositions, and methods. The disclosed embodiments are not intended to be limiting of the claims. To the contrary, the claims are intended to cover all alternatives, modifications, and equivalents.

General Description of Formulations

The pellet cores of the invention comprise one of more active ingredients. The product may include, for example, a single dosage form unit that includes, or consists essentially of, acamprosate and at least one second medication. In one embodiment, the active ingredient includes at least one homotaurine analog selected from the group consisting of: an acetylaminopropane sulfonate, an acetylaminopropane sulfonate salt, taltrimide, and tauromustine. A preferred active ingredient is acamprosate.

Acamprosate and its derivatives can be used as single agents or in combination therapy with mGluR antagonists to treat Autism Spectrum Disorders, Fragile X syndrome, Down's syndrome and other forms of mental retardation. Suitable mGluR antagonists are Group I mGluR antagonists including, for example, 2-methyl-6-(phenylethynyl)-pyridine (MPEP), (E)-6-methyl-2-styrylpyridine (SIB 1893), 6-methyl-2-(phenylazo)-3-pyridinol and a-methyl-4-carboxyphenylglycine (MCPG).

Other Group I mGluR antagonists that can be used as single agents or in combination in the pellet core are described in U.S. Pat. Nos. 6,890,931 and 6,916,821. Yet other suitable mGluR antagonists are mGluR5 antagonists described in WO 01166113, WO 01132632, WO 01/14390, WO 01108705, WO 01/05963, WO 01/02367, WO 01/02342, WO 01102340, WO 00/20001, WO 5 00173283, WO 00/69816, WO 00/63166, WO 00/26199, WO 00/26198, EP-A-0807621, WO 99/54280, WO 99/44639, WO 99/26927 WO 99108678, WO 99102497, WO 98/45270, WO 98/34907, WO 97/48399 WO 97/48400, WO 97/48409, WO 98/53812, WO 96115100, WO 95/25110, WO 98/06724, WO 96/15099 WO 97/05109, WO 97/05137, and U.S. Pat. Nos. 6,218,385, 5,672,592, 5,795,877, 5,863,536, 5,880,112 and 5,902,817.

Other compounds that can be used in combination therapy with acamprosate or singly in the pellet core are antipsychotic agents to treat Fragile X syndrome, Down's syndrome and other forms of mental retardation, or autism. Antipsychotic agents, including atypical antipsychotic compounds for use in combination treatment can include, for example, abaperidone, acetophenazine maleate, alentemol hydrobromide, alpertine, amisulpride, aripiprazole, azaperone, batelapine maleate, benperidol, benzindopyrine hydrochloride, brofoxine, bromperidol, butaclamol hydrochloride, butaperazine, carphenazine maleate, carvotroline hydrochloride, chlorpromazine, chlorprothixene, cinperene, cintriamide, clomacran phosphate, clopenthixol, clopimozide, clopipazan mesylate, cloroperone hydrochloride, clothiapine, clothixamide maleate, clozapine, cyclophenazine hydrochloride, droperidol, etazolate hydrochloride, fenimide, flucindole, flumezapine, fluphenazine decanoate, fluphenazine enanthate, fluphenazine hydrochloride, fluspiperone, fluspirilene, flutroline, gevotroline hydrochloride, halopemide, haloperidol, iloperidone, imido line hydrochloride, lenperone, loxapine, lithium, mazapertine succinate, mesoridazine, metiapine, milenperone, milipertine, molindone hydrochloride, naranol hydrochloride, neflumozide hydrochloride, nemonapride, ocaperidone, olanzapine, oxiperomide, penfluridol, pentiapine maleate, perospirone, perphenazine, pimozide, pinoxepin hydrochloride, pipamperone, piperacetazine, pipotiazine palmnitate, piquindone hydrochloride, prochlorperazine edisylate, prochlorperazine maleate, promazine hydrochloride, quetiapine, remoxipride, remoxipride hydrochloride, risperidone, rimcazole hydrochloride, riluzole, seperidol hydrochloride, sertindole, setoperone, spiperone, sulpiride, thioridazine, thiothixene, thorazine, tioperidone hydrochloride, tiospirone hydrochloride, trifluoperazine hydrochloride, trifluperidol, triflupromazine, ziprasidone hydrochloride, zotepine, zuclopenthixol, as well as analogs, derivatives and combinations thereof.

Other compounds can be used in combination therapy with acamprosate or in singly in the pellet core that include a antipsychotic (neuroleptic) medication, a selective serotonin reuptake inhibitor (SSRI), a serotonin-norepinephrine reuptake inhibitor (SNRI), an antidepressant, an anti-anxiety medication, or the like. The antipsychotic medication can be, for example, a first or a second generation antipsychotic. The first or a second generation antipsychotic can be for example, one or more of thioridazine, chlorpromazine, thiothixene, trifluoperazine, fluphenazine, haloperidol, perphenazine, loxapine, molindone, metoclopramide, aripiprazole, asenapine, iloperidone, lurasidone, olanzapine, paliperidone, quetiapine, risperidone, ziprasidone, and the like. The SSRI or SNRI can be, for example, one or more of citalopram, desvenlafaxine, doxepin, duloxetine, escitalopram, fluoxetine, fluvoxamine, milnacipran, paroxetine, sertraline, venlafaxine, and the like.

In other embodiments, compounds of acamprosate calcium can be used singly or in combination therapy with at least one compound selected from the group consisting of the $GABA_A$ agonist bamaluzole, D-Cycloserine, GABA, gabamide, GABOB, gaboxadol, ibotenic acid, isoinpecotic acid, muscimol, phenibut, picamilon, progabide, SL75102, Thiomuscimol, and positive allosteric modulators that increase the activity of $GABA_A$ such as alcohols, alprazolam, barbiturates, benzodiazepines and nonbenzodiazepines.

In other embodiments, compounds of acamprosate calcium can be used singly or in combination therapy with at least one compound selected from the group consisting of a $GABA_B$ receptor agonist, a muscarinic receptor antagonist, a stimulant, a nicotinic receptor agonist, an endocannabinoid receptor antagonist, an AMPA agonist, an antidepressant, an a2-adrenergic agonist, or an anticonvulsant to treat Fragile X syndrome, Down's syndrome and other forms of mental retardation, or autism. In some embodiments, the $GABA_B$ receptor agonist is baclofen, R-baclofen, or a prodrug thereof, for example as disclosed in U.S. Pat. Nos. 7,109,239 and 7,300,956. In other embodiments, the muscarinic receptor antagonist is atropine, benztropine, biperiden, dicyclomine, ipratroprium, procyclidine, scopolamine, tiotropium, telenzepine or trihexyphenidyl. In other embodiments, the stimulant is amantadine, bupropion, atomoxetine, dextroamphetamine, modafinil, caffeine, methylphenidate, nicotine, pseudoephedrine, and amphetamine, as well as metabolites, isomers or prodrugs thereof.

The active compound is preferably homogeneously dispersed in the core and is released with a delay after the surrounding enteric coating is dissolved. The pellet cores of the invention may comprise any acceptable diluent, such as Acacia, Gelatin, Hydroxypropyl cellulose, Hydroxypropylmethyl cellulose, Methylcellulose, Polyetylene glycol (PEG), Povidone, Sucrose, Starch, or a mixture of any of these. Methylcellulose is a preferred diluent.

The pellets of the invention include a coating comprising a release-modifying agent, such as ethyl cellulose, carnauba wax, shellac, or a mixture of any of these. Ethyl cellulose is preferred.

The enteric coating of the pellets of the invention should only dissolve after the formulation has left the stomach. Such coatings are disclosed in the prior art (e.g., EP 0 453 001 A1). Preferred enteric coatings according to the invention comprise a methacrylic acid copolymer or methylhydroxypropylcellulose phthalate. Poly(methacrylic acid, methyl methacrylates), which are obtainable under the tradenames Eudragit® L or S and have free carboxyl groups as functional groups, are preferred. These polymers are insoluble in the gastric juice, but dissolve in digestive juices above pH 5.5-7 depending on the number of functional carboxyl groups. Poly(methacrylic acid, methyl methacrylate) 1:1 (Eudragit® L 100; methacrylic acid copolymer, USP/NF type A) and poly(methacrylic acid, methyl methacrylate) 1:2 (Eudragit® S; methacrylic acid copolymer, USP/NF type B) are particularly preferred. Eudragit® L 100 is the most preferred. Mixtures of the coating materials mentioned, in particular of Eudragit® L and Eudragit® S, can also be used.

The pellet formulations of the invention can optionally contain one or more conventional additives such as lubricants, colorants, flow agents, glidants, fillers, perfumes, flavors, flavor enhancers, such as sweeteners (both artificial and natural), and other conventional pharmaceutical additives, e.g., effervescent agents.

For example, lubricants such as adipic acid, magnesium stearate, calcium stearate, zinc stearate, hydrogenated vegetable oils, sodium chloride, sterotex, polyoxyethylene, glyceryl monostearate, talc, polyethylene glycol, sodium benzoate, sodium lauryl sulfate, magnesium lauryl sulfate, sodium stearyl fumarate, light mineral oil and the like may be employed, with sodium stearyl fumarate preferred. Waxy fatty acid esters, such as glyceryl behenate, sold as "Compritol" products, can be used. Other useful commercial lubricants include "Stear-O-Wet" and "Myvatex TL". Mixtures are operable.

Glidants such as starch, talc, lactose, stearates, dibasic calcium phosphate, magnesium carbonate, magnesium oxide, calcium silicate. Cabosil, Syloid, and silicon dioxide aerogels may be employed.

Fillers may be used, for example, to increase the bulk of the sachet. Some of the commonly used fillers are calcium sulfate, both di- and tri-basic; starch; calcium carbonate; microcrystalline cellulose; modified starches, lactose, sucrose; mannitol; and sorbitol.

Flavors may be chosen from natural and synthetic flavoring liquids. An illustrative list of such agents includes volatile oils, synthetic flavor oils, flavoring aromatics, oils, liquids, oleoresins and extracts derived from plants, leaves, flowers, fruits, stems and combinations thereof. A non-limiting representative list of these includes citric oils, such a lemon, orange, grape, lime and grapefruit an fruit essences, including apple, pear, peach, grape, strawberry, raspberry, cherry, plum, pineapple, apricot, or other fruit flavors. Other useful flavorings include aldehydes and esters, such as benzaldehyde (cherry, almond); citral, i.e., alpha-citral (lemon, lime); neral, i.e., beta-citral (lemon, lime); decanal (orange, lemon); aldehyde C-8 (citrus fruits); aldehyde C-9 (citrus fruits); aldehyde C-12 (citrus fruits); tolyl aldehyde (cherry, almond); 2,6-dimethyloctanal (green fruit); 2-dodedenal (citrus, mandarin); mixtures thereof and the like.

Sweeteners may be chosen from the following non-limiting list: glucose (corn syrup), dextrose, invert sugar, fructose, and mixtures thereof (when not used as a carrier); saccharin and its various salts, such as the sodium salt; dipeptide sweeteners such as aspartame; dihydro-chalcone compounds, glycyrrhizin; *Stevia Rebaudiana* (Stevioside); chloro derivatives or sucrose such as sucralose; and sugar alcohols such as sorbitol, mannitol, xylitol, and the like. Also contemplated are hydrogenated starch hydrolysates and the synthetic sweeteners such as 3,6-dihydro-6-methyl-1-1-1,2,3-oxathiazin-4-one-2,2-dioxide, particularly the potassium salt (acesulfame-K), and sodium and calcium salts thereof.

Some embodiments include effervescent agents to aid in masking the objectionable taste of active ingredients, such as vitamins, medicines and/or minerals, etc. The positive organoleptic sensation achieved by the effervescent action in the mouth, as well as the texture, speed and sensation of disintegration, aid in masking undesirable flavor notes.

Color additives can be used. Such color additives include food, drug and cosmetic colors (FD&C), drug and cosmetic colors (D&C) or external drug and cosmetic colors (Ext. D&C). These colors are dyes, lakes, and certain natural and derived colorants. Useful lakes include dyes absorbed on aluminum hydroxide or other suitable carriers.

Pharmaceutical compositions provided by the present disclosure may be practiced with dosage forms adapted to provide sustained release of an active ingredient upon oral administration. Sustained release oral dosage forms may be used to release drugs over a prolonged time period and are useful when it is desired that a drug or drug form be delivered to the lower gastrointestinal tract. Sustained release oral dosage forms include any oral dosage form that maintains therapeutic concentrations of a drug in a biological fluid such as the plasma, blood, cerebrospinal fluid, or in a tissue or organ for a prolonged time period. Sustained release oral dosage forms include diffusion-controlled systems such as reservoir devices and matrix devices, dissolution-controlled systems, osmotic systems, and erosion-controlled systems. Sustained release oral dosage forms and methods of preparing the same are well known in the art.

Regardless of the specific type of controlled release oral dosage form used, an active ingredient may be released from an orally administered dosage form over a sufficient period of time to provide prolonged therapeutic concentrations of an active ingredient in the plasma and/or blood of a subject. Following oral administration, a dosage form comprising an active ingredient may provide a therapeutically effective concentration of the corresponding drug in the plasma and/or blood of a subject for a continuous time period, e.g., for at least about 4 hours, for at least about 8 hours, for at least about 12 hours, for at least about 16 hours, and in certain embodiments, for at least about 20 hours following oral administration of the dosage form to the subject. The continuous time periods during which a therapeutically effective concentration of the drug is maintained may be the same or different. The continuous period of time during which a therapeutically effective plasma concentration of the drug is maintained may begin shortly after oral administration or following a time interval.

An appropriate dosage of an active ingredient or pharmaceutical composition comprising an active ingredient may be determined according to any one of several well-established protocols. For example, animal studies such as studies using mice, rats, dogs, and/or monkeys may be used to determine an appropriate dose of a pharmaceutical compound. Results from animal studies may be extrapolated to determine doses for use in other species, such as for example, humans.

Uses of Formulations

In some embodiments, this disclosure is directed to acamprosate oral pellet formulations in the manufacture of a medicament for use in methods of treatment of any neurotransmission or cognitive disorder that is characterized as a glutamate-GABA imbalance, any disorder characterized with disrupted or dysregulated ERK signaling pathway or rasopathies resulting in abnormalities in brain development, learning, memory and cognition. These include, but are not limited to, Autism Spectrum Disorders, Pervasive Development Disorders—Not Otherwise Specified, Idiopathic Autism, Fragile X Syndrome, Asperger's Syndrome, Rhett's Syndrome, Childhood Disintegrative Disorder as further referenced in Diagnostic and Statistical Manual of Mental Disorders V, Alcohol dependence, tinnitus, sleep apnea, Parkinson's Disease, levodopa-induced dyskinesias in Parkinson's Disease, Alzheimer's Disease, Huntington's Disease, Amyotrophic Lateral Sclerosis, Cortical spreading depression, migraine, schizophrenia, anxiety, tardive dyskinesia, spasticity, multiple sclerosis, various types of pain, or binge eating, subjects having or at risk for age-related cognitive impairment, Mild Cognitive Impairment (MCI), dementia, Alzheimer's Disease (AD), prodromal AD, post-traumatic stress disorder (PTSD), bipolar disorder, amyotrophic lateral sclerosis (ALS), cancer-therapy-related cognitive impairment, drug induced or toxin induced cognitive impairments, compulsive behavior, and substance addiction.

Also provided herein are methods of treating a subject with Fragile X syndrome, Autism Spectrum Disorders, Down's syndrome, a neurological disorder and/or mental retardation in order to diminish, halt, ameliorate or prevent one or more of the neurological deficiencies or symptoms associated with the disorder (e.g., benign childhood epilepsy, temporal lobe epilepsy, visual spatial defects, anxiety, aggression, hyperactivity, agitation, repetitive behaviors, abnormal or limited social interactions, language and learning difficulties, and/or combinations thereof). In certain embodiments, children with mental retardation, Autism Spectrum Disorders, Down's Syndrome and Fragile X Syndrome can be treated with a formulation of the invention. The children can be treated during infancy (between about 0 to about 1 year of life), childhood (the period of life between infancy and puberty) and during puberty (between about 8 years of life to about 18 years of life).

In certain embodiments, the methods disclosed herein can be used to treat adults (greater than about 18 years of life) having mental retardation, Fragile X Syndrome, Autism Spectrum Disorders and/or Down's Syndrome. In certain embodiments, anxiety and epilepsy in subjects (both children and adults) having Fragile X Syndrome, Autism Spectrum Disorders, mental retardation and/or Down's syndrome can be treated by administering to the subjects a formulation of the invention.

Dosing and Administration

The amount of an active ingredient that will be effective in the treatment of a disease in a subject will depend, in part, on the nature of the condition and can be determined by standard clinical techniques known in the art. In addition, in vitro or in vivo assays may be employed to help identify optimal dosage ranges. A therapeutically effective amount of an active ingredient to be administered may also depend on, among other factors, the subject being treated, the weight of the subject, the severity of the disease, the manner of administration, and the judgment of the prescribing physician.

The unit dose of the drug is generally about 100) mg to about 2500 mg. Preferably, the unit dose is about 200 to about 500 mg (e.g., about 333 mg). The unit dose form is typically administered 1-4 times per day, preferably 2-3 times per day.

The pellet formulations of the invention are typically intended for oral administration. For example, the pellets can be packaged in sachets, which are opened at the time of use, and the drug product sprinkled onto food for ingestion. Preferred foods have a pH of less than about 5.5, such as applesauce and yogurt. The pellets can also be encased in a capsule, which can either be taken as such, or the capsule can be opened and the contents sprinkled onto food for ingestion.

Examples

It is an objective of the present invention to develop Acamprosate Calcium enteric-coated pellets for sprinkle dosage form and establish the stability of these prototype sprinkles packaged in aluminum pouches/sachets. The target product attributes of the Acamprosate Sprinkles dosage form are summarized in Table 1.

TABLE 1

| Acamprosate sprinkles target drug product attributes | |
| --- | --- |
| Dosage form | Sprinkles |
| Strength | 333 mg |
| Packaging configuration | Packaged in aluminum sachets |
| Informal stability study | To be evaluated at 25° C./60% RH up to 6 months 40° C./75% RH up to 6 months |

The API is known to cause GI irritation and the two current marketed formulations are an enteric-coated tablet, Campral (Campral is manufactured and marketed in the United States by Forest Laboratories, while Merck KGaA markets it outside the US) and Acampral (Sun Pharmaceuticals). The formulation development approach was to manufacture the pellets sprinkles and coating with an enteric polymer to avoid or minimize the release of API into the stomach when administered orally. The objectives involved manufacture of pellets of Acamprosate Calcium, with suitable excipient and coating of pellets, to optimize drug release along with shelf stability evaluation of two different sizes/diameters. Sprinkles with two different sizes/diameters were designed with further down-selection to a preferred size/diameter based the drug release profile.

The properties of the drug substance from different lots used in the formulation development are summarized in Table 2. The excipients mentioned in Table 3 were used for sprinkles formulation development trials.

TABLE 2

| Properties of Acamprosate calcium drug substance | | | | | |
| --- | --- | --- | --- | --- | --- |
| Batch/Lot No. | Batch description | Appearance | Assay (% w/w) | Particle size ($d_{90}$ in μm) | CoA |
| F041020015 | Procured from IndSwift | White powder | 100.0 | 133 | Annexure 1 |
| F041020016 | Procured from IndSwift | Almost white powder | 99.5 | 149 | Annexure 2 |

TABLE 3

| List of excipients used for Acamprosate calcium sprinkles | | | | | |
| --- | --- | --- | --- | --- | --- |
| S. No | Ingredients | Functional category | Lot/Batch. No. or A R. No | Manufacturer | Compendial grade |
| 1 | Acamprosate calcium | Active ingredient | F041020015/ | Ind Swift | Ph. Eur |
| 2 | Microcrystalline cellulose (Avicel PH 101) | Diluent | 61418C | FMC Biopolymer | USPNF/ |
| 4 | Ethyl cellulose (Ethocel Standard 20 premium) | Sustain release agent | GA374542 | Colorcon | USP |
| 5 | Triethyl citrate | Plasticizer | K43383059 | Merck | USP/NF |
| 6 | Talc | Anti-tacking agent | S191/13 | Luzenac | USP/NF |
| 7 | Eudragit L 100 55 | Enteric coating polymer | B130404014 | Evonik | Ph. Eur/USP |

The details of equipment used for formulation and analytical development of Acamprosate Calcium sprinkles is shown in Table 4.

TABLE 4

Details of equipment used for Acamprosate calcium sprinkles development

| S. No. | Equipment | Manufacturer | Model |
|---|---|---|---|
| 1 | Extruder and Spheronizer | Umang Pharma | NA |
| 1 | Analytical balance | Sartorius | GP5205 |
| 2 | Stability chambers | WiseCube, Wisdom Laboratory Instruments | TEMI850 |
| 3 | Dissolution system | Lab India | DS-8000 |
| 4 | GPCG 1.1 | Glatt | GPCG 1.1 |

The analytical methods used for evaluation of sprinkles, such as assay and dissolution methods are summarized in Tables 5-7.

TABLE 5

Assay method details for Acamprosate Calcium sprinkles

| Parameter | | |
|---|---|---|
| Assay | Buffer: | TEA (0.5%) pH adjusted to 4.0 |
| | Mobile phase: | Buffer |
| | Diluent: | Milli Q Water |
| | Chromatographic System: | LC |
| | Detector: | 210 nm |
| | Column: | Cosmosil 5C18-PAQ (4.6*250 mm, 5μ) (C18) |
| | Flow rate: | 0.7 mL/min |
| | Retention Time: | 20 min |
| | Column Temp: | 25° C. |

TABLE 6

Related substances method details for Acamprosate Calcium sprinkles

| Parameter | | |
|---|---|---|
| Impurity A | Buffer: | KH$_2$PO$_4$ adjusted the pH to 6.5 |
| | Diluent: | Borate buffer solution pH 10.4 |
| | Mobile phase: | Buffer:Acetonitrile:Methanol (80:10:10) |
| | Sample preparation: | Fluoresacmine derivatization |
| | Chromatographic System: | LC |
| | Detector: | 261 nm |
| | Column: | Discovery HS C18, 15 cm*4.6 mm, 3 μm |
| | Flow rate: | 1 ml/min |
| | Retention Time: | 60 min |
| Other Impurities | Buffer: | TEA (0.5%) pH adjusted to 4.0 |
| | Mobile phase: | Buffer |
| | Diluent: | Milli Q water |
| | Chromatographic System: | LC |
| | Detector: | 210 nm |
| | Column: | Cosmosil 5C18-PAQ (4.6*250 mm, 5 μm) |
| | Flow rate: | 0.7 ml/min |
| | Retention Time: | 60 min |
| | Column temperature: | 25° C. |
| | Total impurities: | Method A + Method B impurities |

TABLE 7

Dissolution method details for Acamprosate Calcium sprinkles

| | |
|---|---|
| Dissolution medium | pH 1.2 for 2 hours followed by pH 6.8 for 3 hours |
| Apparatus | USP-II (Paddle) |
| Temperature | 37° C. ± 0.5° C. |

Two different marketed enteric-coated tablets were evaluated for dissolution, and the details of the products and dissolution results are presented in Tables 8 and 9.

TABLE 8

Dissolution of ACAMPROL 333 mg Tablet

| Tablet | pH 1.2 | pH 6.8 citrate buffer, Basket, 180 RPM | | | | |
|---|---|---|---|---|---|---|
| No. | 120 min | 30 min | 60 min | 90 min | 120 min | 180 min |
| 1 | 0 | 46 | 70 | 89 | 90 | 91 |
| 2 | 1 | 44 | 63 | 81 | 89 | 95 |
| 3 | 0 | 66 | 87 | 93 | 95 | 96 |
| AVG | 0 | 52 | 73 | 88 | 91 | 94 |
| STDEV | 0.6 | 12.2 | 12.3 | 6.1 | 3.2 | 2.6 |
| RSD | 0.00 | 23.46 | 16.85 | 6.93 | 3.52 | 2.77 |

TABLE 9

Dissolution of CAMPRAL 333 mg Tablet (Batch No - A416140)

| Tablet | pH 1.2 | pH 6.8 citrate buffer, Basket, 180 RPM | | | | |
|---|---|---|---|---|---|---|
| No. | 120 min | 30 min | 60 min | 90 min | 120 min | 180 min |
| 1 | 0 | 30 | 73 | 93 | 99 | 99 |
| 2 | 0 | 28 | 67 | 89 | 99 | 99 |
| 3 | 0 | 27 | 62 | 87 | 98 | 98 |
| AVG | 0 | 28 | 67 | 90 | 99 | 99 |
| STDEV | 0.0 | 1.5 | 5.5 | 3.1 | 0.6 | 0.6 |
| RSD | 0 | 5.36 | 8.21 | 3.44 | 0.61 | 0.61 |

The dissolution results of the marketed products indicated that negligible or zero drug release occurred in pH 1.2 buffer, and complete release in pH 6.8 buffer. A difference was observed in the release profile between the two marketed tablets over the first 30 min.

1. Acaworosate Calcium Enteric-Coated Sprinkles: (1$^{st}$ Generation Studies)

It is a further objective of the present invention to develop a sprinkle formulation to achieve <10% release (as close to zero drug release as possible) in pH 1.2 buffer and complete release in pH 6.8 buffer, as compared to the marketed products. Sprinkles with two different sizes (#16/20 and #25/30) were manufactured to down-select one format based on the drug release profile (dissolution).

Manufacture of Acamprosate Calcium Sprinkles (#16/20 ASTM)

The formula composition for the manufacture of sprinkles is shown in Table 10. The sprinkles were manufactured by extrusion of wet mass of API+Avicel PH 101 through a mesh size of 1.2 mm. The extruded material was charged into a spheronizer at plate RPM of 2.1 for 10 min to obtain spherical shaped sprinkles.

TABLE 10

Composition of Acamprosate calcium sprinkles (B. No. SF14000746)

| S. No. | Composition | Category | g/batch |
|---|---|---|---|
| 1 | Acamprosate calcium* | Active | 500 |
| 2 | Avicel PH 101 | Diluent | 500 |
|  | Total |  | 1000 g |

The assay and dissolution was conducted for the sprinkle formulation. Each 200 mg of sprinkles were equivalent to 100 mg of Acamprosate Calcium API. Assay of sprinkles: 98.0% w/w.

TABLE 11

Dissolution of Acamprosate Calcium sprinkles in pH 6.8 buffer

|  | 30 min | 60 min | 90 min | 120 min | 180 min | Infinity |
|---|---|---|---|---|---|---|
| AVG (n = 3) | 98 | 98 | 99 | 99 | 99 | 99 |
| STDEV | 1.7 | 1.0 | 1.0 | 1.2 | 1.2 | 1.0 |
| RSD | 1.73 | 1.02 | 1.01 | 1.21 | 1.21 | 1.01 |

As shown in Table 11, the complete drug release observed in the first 30 min indicated that release control (sustained release) was required in order achieve drug release for a period up to 3 hours as compared to marketed products. Hence, ethyl cellulose coating of up to 20% on the sprinkles was considered to sustain the drug release in pH 6.8 buffer followed by enteric coating. The formula composition for ethyl cellulose sustained-release coating is shown in Table 12, and the manufacturing procedure for the ethyl cellulose coating is shown in Table 13.

TABLE 12

Formula composition for Ethyl cellulose coating (B. No. SF14000938)

| Ingredients | % w/w weight gain | Quantity in g for 200 g batch size |
|---|---|---|
| Ethyl cellulose 20 standard premium | — | 38.4 g |
| Triethyl citrate | 25% | 9.6 g |
| IPA:Purified water | 1:1 | QS |

TABLE 13

Manufacturing procedure for Ethyl cellulose coating

| Solution preparation | Machine Controls (GPCG 1.1 bottom spray) |
|---|---|
| Solution prepared for 20% W/W weight gain | Nozzle diameter - 0.8 mm |
| Overages considered for 20% W/W weight gain | Bottom Plate - Type C |
| Ethyl cellulose added into IPA:water solution with stirring | Inlet Temperature - 35° C.-50° C. |
| Triethyl citrate added into Ethyl cellulose solution | Product Temperature - 30° C.-40° C. |
| Solution is passed through ASTM 60# mesh before using it for coating | Exhaust Temperature - 40° C.-50° C. |

Ethyl cellulose coated sprinkles are further coated with Eudragit L 100 55 polymer for enteric protection. The formula composition for the enteric coating is shown in Table 14, and the manufacturing procedure for the enteric coating is shown in Table 15

TABLE 14

Formula composition for enteric coating (B. No. SF14000938)

| Ingredients | % w/w weight gain | Quantity in G for 200 g batch size |
|---|---|---|
| Eudragit L 100 55 | — | 68.57 g |
| Triethyl citrate | 25 | 17.14 |
| Talc | 50 | 34.28 |
| Acetone:IPA:Purified water (Diluent) | 38.1:57.13:4.77 | QS |

TABLE 15

Manufacturing procedure for enteric coating

| Solution preparation | Machine Controls (GPCG 1.1 bottom spray) |
|---|---|
| Solution prepared for 50% W/W weight gain | Nozzle diameter - 1.2 mm |
| Overages considered for 20% W/W weight gain | Bottom Plate - Type C |
| Eudragit L100 55 was added into 50% of the diluent under stirring | Inlet Temperature - 25° C.-35° C. |
| Talc and Triethyl citrate were added into 50% of the diluent under Homogenizer | Product Temperature - 25° C.-30° C. |
| Homogenized suspension was added into Eudragit L 100 55 under stirring | Exhaust Temperature - 30° C.-40° C. |
| Solution is passed through ASTM 60# mesh before using it for coating |  |

The dissolution results of Acamprosate Calcium enteric-coated sprinkles (25% w/w) in pH 1.2 followed with pH 6.8 buffer are shown in Table 16. 300 mg of sprinkles equivalent to 100 mg of Acamprosate Calcium API. Assay: 105.2% w/w

TABLE 16

Dissolution of 25% enteric-coated sprinkles
Batch Number: SF14000938 (#16/20 ASTM sprinkles)
Coating percentage: 25% W/W Enteric-coated sprinkles (Eudragit L100 55)

|  | Acid Stage pH 1.2 | | | | Buffer Stage pH 6.8 | | | | |
|---|---|---|---|---|---|---|---|---|---|
|  | 15 min | 30 min | 60 min | 120 min | 30 min | 60 min | 90 min | 120 min | 180 min |
| 1 | 1 | 3 | 8 | 23 | 62 | 72 | 79 | 84 | 90 |
| 2 | 1 | 3 | 7 | 21 | 59 | 68 | 75 | 81 | 87 |
| 3 | 0 | 2 | 5 | 17 | 53 | 64 | 71 | 76 | 84 |
| AVG | 1 | 3 | 7 | 20 | 58 | 68 | 75 | 80 | 87 |

The drug release of 20% in pH 1.2 buffer for enteric-coated sprinkles indicated that the 25% coating was not sufficient to control the drug release to <10%. Hence, a higher percentage of eudragit coating, such as 50% was considered.

The dissolution results of Acamprosate calcium enteric-coated sprinkles (50% w/w) in 10 pH 1.2 followed with pH 6.8 buffer are shown in Table 17. 360 mg of sprinkles equivalent to 100 mg of Acamprosate calcium API. Assay: 108.5%.

TABLE 17

Dissolution of 50% enteric-coated sprinkles
Batch Number: SF14000938 (#16/20 ASTM sprinkles)
Coating percentage: 50% W/W Enteric-coated sprinkles (Eudragit L100 55)

| | Acid Stage pH 1.2 | | | | Buffer Stage pH 6.8 | | | | |
|---|---|---|---|---|---|---|---|---|---|
| | 15 min | 30 min | 60 min | 120 min | 30 min | 60 min | 90 min | 120 min | 180 min |
| 1 | 0 | 0 | 1 | 4 | 46 | 58 | 67 | 73 | 81 |
| 2 | 0 | 0 | 1 | 4 | 46 | 59 | 68 | 74 | 82 |
| 3 | 0 | 0 | 1 | 3 | 45 | 57 | 65 | 72 | 80 |
| AVG | 0 | 0 | 1 | 4 | 46 | 58 | 67 | 73 | 81 |

The target drug release of <10% in pH 1.2 buffer was achieved for the sprinkles with 50% w/w enteric coating. Hence 50% enteric coating was considered preferred.

Manufacture of Acamprosate Calcium Sprinkles #25/30 ASTM Mesh Size

The smaller size sprinkles were also manufactured using API and Avicel PH 101 similar to bigger size sprinkles at 1:1 mixture. The mesh size for smaller sprinkles was 0.8 mm as compared to 1.2 mm for the larger sprinkles.

The Formula composition for the 20% ethyl cellulose sustained release coating is shown in Table 18, and the manufacturing procedure in Table 19.

TABLE 18

Formula composition for Ethyl cellulose coating (B. No. SF14000999)

| Ingredients | % w/w weight gain | Quantity in g for 200 g batch size |
|---|---|---|
| Ethyl cellulose 20 standard premium | — | 38.4 g |
| Triethyl citrate | 25% | 9.6 g |
| IPA:Purified water | 1:1 | QS |

TABLE 19

Manufacturing procedure for Ethyl cellulose coating

| Solution preparation | Machine Controls (GPCG 1.1 bottom spray) |
|---|---|
| Solution prepared for 20% W/W weight gain | Nozzle diameter - 0.8 mm |
| Overages considered for 20% W/W weight gain | Bottom Plate - Type C |
| Ethyl cellulose added into IPA:water solution with stirring | Inlet Temperature - 35° C.-50° C. |
| Triethyl citrate added into Ethyl cellulose solution | Product Temperature - 30° C.-40° C. |
| Solution is passed through ASTM 60# mesh before using it for coating | Exhaust Temperature - 40° C.-50° C. |

The dissolution results for ethyl cellulose coated sprinkles (20% w/w) is shown in Table 20. 300 mg of sprinkles equivalent to 100 mg of Acamprosate calcium API. Assay: 103.5% w/w.

TABLE 20

Dissolution of 20% ethyl cellulose coated sprinkles
Batch Number: SF14000999 (#25/30 ASTM sprinkles)
Coating percentage: 20% W/W ethyl cellulose coating

| | Acid Stage pH 1.2 | | | | Buffer Stage pH 6.8 | | | | | | |
|---|---|---|---|---|---|---|---|---|---|---|---|
| | 15 min | 30 min | 60 min | 120 min | 30 min | 60 min | 90 min | 120 min | 180 min | 300 min | 24 h |
| Avg | 4 | 12 | 27 | 51 | 61 | 67 | 71 | 75 | 79 | 89 | 103 |
| Stdev | 0.6 | 1.0 | 2.0 | 1.7 | 2.5 | 2.6 | 2.5 | 2.1 | 2.1 | 1.5 | 0.6 |
| RSD | 15.00 | 8.33 | 7.41 | 3.33 | 4.10 | 3.88 | 3.52 | 2.80 | 2.66 | 1.69 | 0.58 |

The drug release was found to be 90% after 5 hours and complete release after the end of 24 hours indicting that 100% drug is present in sprinkles.

The sprinkles were then used for enteric coating. The formula composition of the enteric coating is shown in Table 21, and the manufacturing procedure in Table 22.

TABLE 21

Formula composition for enteric-coating (B. No. SF14000999)

| Ingredients | % w/w weight gain | Quantity in G for 200 g batch size |
|---|---|---|
| Eudragit L 100 55 | — | 68.57 g |
| Triethyl citrate | 25 | 17.14 |
| Talc | 50 | 34.28 |
| Acetone:IPA:Purified water (Diluent) | 38.1:57.13:4.77 | QS |

TABLE 22

Manufacturing procedure for enteric coating

| Solution preparation | Machine Controls (GPCG 1.1 bottom spray) |
|---|---|
| Solution prepared for 50% W/W weight gain | Nozzle diameter - 1.2 mm |
| Overages considered for 20% W/W weight gain | Bottom Plate - Type C |
| Eudragit L100 55 was added into 50% of the diluent under stirring | Inlet Temperature - 25° C.-35° C. |
| Talc and Triethyl citrate were added into 50% of the diluent under Homogenizer | Product Temperature - 25° C.-30° C. |
| Homogenized suspension was added into Eudragit L 100 55 under stirring | Exhaust Temperature - 30° C.-40° C. |
| Solution is passed through ASTM 60# mesh before using it for coating | |

The dissolution results of Acamprosate calcium enteric-coated sprinkles (50% w/w) in pH 1.2 followed with pH 6.8 buffer are shown in Table 23. 360 mg of sprinkles equivalent to 100 mg of Acamprosate calcium API. Assay: 103.5%

TABLE 23

Dissolution of 50% enteric-coated sprinkles
Batch Number: SF14000999 (#25/30 ASTM sprinkles)
Coating percentage: 50% W/W Enteric-coated sprinkles (Eudragit L100 55)

| | Acid Stage pH 1.2 | | | | Buffer Stage pH 6.8 | | | | | |
|---|---|---|---|---|---|---|---|---|---|---|
| | 15 min | 30 min | 60 min | 120 min | 30 min | 60 min | 90 min | 120 min | 180 min | 300 min |
| Avg | 0 | 0 | 0 | 3 | 44 | 59 | 71 | 77 | 85 | 107 |
| Stdev | 0.0 | 0.0 | 0.6 | 0.0 | 3.5 | 2.6 | 3.1 | 2.5 | 1.5 | 0.6 |
| RSD | 0 | 0 | 0 | 0.00 | 7.95 | 4.41 | 4.37 | 3.25 | 1.76 | 0.56 |

The target drug release of <10% in pH 1.2 buffer was achieved for the sprinkles with 50% w/w enteric coating. Hence, 50% enteric coating was considered preferred for smaller size sprinkles as well. There was no notable difference in the dissolution and assay of sprinkles of #16/20 and #25/30 ASTM.

The sprinkles are intended to be administered in an edible matrix, such as applesauce or yogurt. Most brands of applesauce have a pH in the range of 3-3.6. To determine the drug release in pH 3.0 and 4.5, a dissolution study was conducted on the sprinkles, and the results are shown in Tables 24 and 25.

TABLE 24

Dissolution of 50% enteric-coated sprinkles in pH 3.0 buffer

| | 30 min | 60 min | 120 min | 180 min |
|---|---|---|---|---|
| Sample 1 | 0 | 0 | 0 | 1 |
| Sample 2 | 0 | 0 | 0 | 2 |
| Sample 3 | 0 | 0 | 0 | 1 |
| Avg | 0 | 0 | 0 | 1 |
| Stdev | 0.0 | 0.0 | 0.0 | 0.6 |
| RSD | 0 | 0 | 0 | 60.00 |

TABLE 25

Dissolution of 50% enteric-coated sprinkles in pH 4.5 buffer

| | 30 min | 60 min | 120 min | 180 min |
|---|---|---|---|---|
| Sample 1 | 0 | 0 | 1 | 2 |
| Sample 2 | 0 | 0 | 1 | 3 |
| Sample 3 | 0 | 0 | 1 | 2 |
| Avg | 0 | 0 | 1 | 2 |
| Stdev | 0 | 0 | 0 | 0.6 |
| RSD | 0 | 0 | 0 | 30.00 |

Drug release of sprinkles in pH 3.0 and 4.5 was observed to be NMT 2% after 120 min Stability Study of #25/30 Sprinkles The prototypes were placed on stability and details of the study is mentioned below Batch No.: SF14000999

Packaging: Sprinkles were weighed into aluminum sachets and sealed.

Fill weight: 1080 mg sprinkles of batch number SF14000999

(Sprinkles weighed equivalent to 300 mg Acamprosate calcium API)

Conditions: 25° C./60% RH & 40° C./75% RH

Time points: Initial, 1, 3 & 6 months

Evaluation: Assay, related substances and dissolution

The results of the stability study of the initial prototype are summarized in Tables 26 and 27, and the dissolution profile in FIG. 1.

TABLE 26

Assay and dissolution results of Acamprosate calcium sprinkles at 40° C./75% RH
Batch Number - SF14000999 (Storage condition - 40° C./75% RH)

| | Time Interval | | | | | | |
|---|---|---|---|---|---|---|---|
| | Initial | | 1 Month | | 3 Month | | 6 Months |
| Assay (%) | 103.51% | | 98.79% | | 107.0% | | 100.0% |

| | Dissolution | | | | | | | |
|---|---|---|---|---|---|---|---|---|
| Time | AVG (N = 3) | RSD (%) | AVG (N = 3) | RSD (%) | AVG (N = 3) | RSD (%) | AVG (N = 3) | RSD (%) |
| 120 min (pH 1.2 buffer) | 3 | 0 | 3 | 20 | 0 | 0 | 3 | 0 |

| Dissolution in pH 6.8 buffer | | | | | | | | |
|---|---|---|---|---|---|---|---|---|
| 30 min | 44 | 7.95 | 66 | 4.70 | 74 | 4.73 | 88 | 0 |
| 60 min | 59 | 4.41 | 79 | 5.32 | 87 | 4.14 | 100 | 0.6 |
| 90 min | 71 | 4.37 | 86 | 5.35 | 95 | 2.42 | 104 | 1.15 |
| 120 min | 77 | 3.25 | 90 | 4.67 | 95 | 2.74 | 106 | 1.42 |
| 180 min | 85 | 1.76 | 94 | 5.43 | 98 | 2.35 | 107 | 0.56 |
| 300 min | 107 | 0.56 | 103 | 4.56 | Not done | Not done | Not done | Not done |

TABLE 27

Assay and dissolution results of Acamprosate calcium sprinkles at 25° C./60% RH
Batch Number - SF14000999 (Storage condition - 25° C./60% RH)

| | Time Interval | | |
|---|---|---|---|
| | Initial | 3 Month | 6 Months |
| Assay (%) | 103.51% | 92.3% | 96.2 |

| | Dissolution | | | | | |
|---|---|---|---|---|---|---|
| Time | AVG (N = 3) | RSD (%) | | | | |
| 120 min (pH 1.2 buffer) | 3 | 20 | 3 | 20 | 3 | 20 |

| Dissolution in pH 6.8 buffer | | | | | | |
|---|---|---|---|---|---|---|
| 30 min | 44 | 7.95 | 43 | 2.79 | 50 | 2 |
| 60 min | 59 | 4.41 | 59 | 1.02 | 67 | 2.54 |
| 90 min | 71 | 4.37 | 68 | 0.88 | 72 | 1.67 |
| 120 min | 77 | 3.25 | 74 | 0.81 | 80 | 2.13 |
| 180 min | 85 | 1.76 | 81 | 0.74 | 85 | 0 |
| 300 min | 107 | 0.56 | Not done | Not done | Not done | Not done |

The dissolution profiles of initial 3 and 6 months stability samples at 25° C./60% RH and 40° C./75% RH faster releases over time. Also the related substances results indicate that the pellets are stable for a period up to 6 months at conditions tested. Also, the related substances results indicate that the pellets are stable for a period up to 6 months at conditions tested.

Manufacture of Acamprosate Calcium Sprinkles for Dog PK Studies

Acamprosate calcium enteric-coated sprinkles were manufactured using #25/30 ASTM sprinkles. Coating was performed with 20% ethyl cellulose (sustained release) followed with 50% enteric coating (Eudragit L 100 55) to achieve the targeted dissolution profile. The same coating procedure was followed as shown in previous section for ethyl cellulose and enteric coating including the formula composition. The batch number for the PK batch is SF14001404.

Stability Study of #25/30 Sprinkles (Dog PK Batch)

The prototypes were loaded on stability and details of the study is mentioned below:

Batch No.: SF14001404

Packaging: Sprinkles were weighed into aluminum sachets and sealed.

Fill weight: 1199 mg sprinkles of batch number SF14001404

(Sprinkles weighed equivalent to 333 mg Acamprosate calcium API)

Conditions: 25° C./60% RH & 40° C./75% RH

Time points: Initial, 1, 3 & 6 months

Evaluation: Assay, related substances and dissolution

The initial results of the PK batch prototype is summarized in Table 28.

TABLE 28

Initial results of Acamprosate calcium sprinkles (PK batch)
Batch Number - SF14001404 40° C./75% RH) 25° C./60% RH)

| | Time Interval | | | | | | | |
|---|---|---|---|---|---|---|---|---|
| | Initial | | 1 Month | | 3 Month | | 3 Months | |
| Assay (%) | 98.2% | | 95.3 | | 95.8% | | 96.5 | |

| | Dissolution | | | | | | | |
|---|---|---|---|---|---|---|---|---|
| Time | Avg (n = 3) | RSD (%) | Avg (n = 3) | RSD (%) | Avg (n = 3) | RSD (%) | Avg (n = 3) | RSD (%) |
| 120 min (pH 1.2 buffer) | 2 | 20 | 2 | 30 | 2 | 30 | 4 | 15 |
| Dissolution in pH 6.8 buffer | | | | | | | | |
| 30 min | 26 | 2.31 | 32 | 1.88 | 29 | 7.93 | 26 | 9.62 |
| 60 min | 42 | 1.43 | 49 | 0 | 49 | 3.06 | 40 | 7.75 |
| 90 min | 53 | 1.13 | 60 | 0 | 62 | 4.68 | 51 | 6.08 |
| 120 min | 61 | 0.98 | 68 | 0 | 71 | 2.96 | 58 | 5.52 |
| 180 min | 72 | 1.39 | 78 | 0 | 81 | 2.1 | 67 | 4.78 |

Acamprosate calcium sprinkles manufactured at two different sizes (#16/20 and #25/30) were found to meet the required target product attributes when compared to marketed products. Ethyl cellulose coating at 20% is required to sustain the release over a period of hours and enteric coating to avoid the release in gastric fluid upon oral administration of sprinkles.

2. Acamprosate Calcium Enteric-Coated Sprinkles: (2$^{nd}$ Generation Studies)

It is yet a further object of the invention to develop and optimize the Acamprosate Calcium enteric-coated pellets for sprinkle dosage form with respect to drug load, ethyl cellulose and Eudragit coating percentages, and to establish the stability of these prototype sprinkles packaged in aluminum pouches/sachets.

The properties of the drug substance from different lots used in the formulation development discussed below are summarized in Table 29.

TABLE 29

Properties of Acamprosate calcium drug substance

| Batch/Lot No. | Batch description | Appearance | Assay (% w/w) | Particle size ($d_{90}$ in μm) |
|---|---|---|---|---|
| G041020031 | Procured by IndSwift | White powder | 99.4% | 116 |

The excipients mentioned in Table 30 were used for sprinkles formulation development trials.

TABLE 280

List of excipients used for Acamprosate calcium sprinkles

| S. No | Ingredients | Lot/Batch. No. or A R.No | Manufacturer | Compendial grade |
|---|---|---|---|---|
| 1 | Acamprosate calcium | F041020015/ | Ind Swift | Ph.Eur |
| 2 | Microcrystalline cellulose (Avicel PH 101) | 61418C | FMC Biopolymer | USPNF/ |
| 4 | Ethyl cellulose (Ethocel Standard 20 premium) | GA374542 | Colorcon | USP |
| 5 | Triethyl citrate | K43383059 | Merck | USP/NF |
| 6 | Talc | S191/13 | Luzenac | USP/NF |
| 7 | Eudragit L 100 55 | B130404014 | Evonik | Ph.Eur/USP |

The details of equipment used for formulation and analytical development of Acamprosate Calcium sprinkles is shown in Table 31.

TABLE 31

Details of equipment used for Acamprosate calcium sprinkles development

| S. No. | Equipment | Manufacturer | Model |
|---|---|---|---|
| 1 | Analytical balance | Sartorius | GP5205 |
| 2 | Stability chambers | WiseCube, Wisdom Laboratory Instruments | TEMI850 |
| 3 | Dissolution system | Lab India | DS-8000 |
| 4 | GPCG 1.1 | Glatt | GPCG 1.1 |

The sprinkle dosage form of the first generation studies was evaluated in dog PK study with formulation composition with 50% drug load acamprosate calcium pellets, with 20% ethyl cellulose coating for sustained release and 50% eudragit coating for enteric protection. The pellets were observed in feces of dog, AUC was lower compared to Campral tablets and Tmax was 12-16 h in the dog PK study. Hence, the further development and optimization of sprinkles was focused on increasing the drug load in pellets, lower the ethyl cellulose percentage to expedite the drug release and optimize/lower the enteric coating.

The analytical methods used for evaluation of sprinkles, such as assay, related substances and dissolution methods are summarized in Tables 32-34.

TABLE 32

Assay method details for Acamprosate Calcium sprinkles Parameter

| Assay | Buffer | TEA (0.5%) pH adjusted to 4.0 |
|---|---|---|
| | Mobile phase | Buffer |
| | Diluent | Milli Q Water |
| | Chromatographic System | LC |
| | Detector | 210 nm |
| | Column | Cosmosil 5C18-PAQ (4.6 * 250 mm, 5μ) (C18) |
| | Flow rate | 0.7 mL/min |
| | Retention Time | 20 min |
| | Column Temp | 25° C. |

TABLE 33

Related substances method details for Acamprosate Calcium sprinkles Parameter

| Impurity A | Buffer | $KH_2PO_4$ adjusted the pH to 6.5 |
|---|---|---|
| | Diluent | Borate buffer solution pH 10.4 |
| | Mobile phase | Buffer:Acetonitrile:Methanol (80:10:10) |
| | Sample preparation | Fluorescamine derivatization |
| | Chromatographic System | LC |
| | Detector | 261 nm |
| | Column | Discovery HS C18, 15 cm * 4.6 mm, 3 μm |
| | Flow rate | 1 ml/min |
| | Retention Time | 60 min |
| Other Impurities | Buffer | TEA (0.5%) pH adjusted to 4.0 |
| | Mobile phase | Buffer |
| | Diluent | Milli Q water |
| | Chromatographic System | LC |
| | Detector | 210 nm |
| | Column | Cosmosil 5C18-PAQ (4.6 * 250 mm, 5 μm) |

TABLE 33-continued

Related substances method details for Acamprosate Calcium sprinkles Parameter

| Flow rate | 0.7 ml/min |
|---|---|
| Retention Time | 60 min |
| Column temperature | 25° C. |

TABLE 34

Dissolution method details for Acamprosate Calcium sprinkles

| Dissolution medium | pH 1.2 for 2 hours followed by pH 6.8 for 3 hours |
|---|---|
| Apparatus | USP-II (Paddle) |
| Temperature | 37° C. ± 0.5° C. |

The sprinkles were manufactured by increasing the drug load from 50% to 60% w/w (API:MCC=60:40%) in order to reduce the quantity of excipients and quantity of sprinkles to be administered for each dose. The formula composition for the manufacture of sprinkles is shown in Table 35.

TABLE 35

Composition of Acamprosate calcium sprinkles

| S. No. | Composition | Category | kg/batch |
|---|---|---|---|
| 1 | Acamprosate calcium | Active | 1.5 |
| 2 | Avicel PH 101 | Diluent | 1.0 |
| | Total | | 2.5 kg |

The manufacturing procedure for the sprinkles includes an extrusion phase followed by a spheronization phase, outlined as follows:

Extrusion
  Step 1: Acamprosate and Avicel PH 101 were mixed in a bowl in 60:40 ratio.
  Step 2: water was added gradually to prepare a damp mass
  Step 3: Damp mass was passed through extruder at 100 rpm extruder speed with 0.8 mm single cone screen
  Step 4: extrudes were further taken for spheronization Spheronization
  Step 1: 2.11 mm check plate was used in the spheronization.
  Step 2: Collected extrudes were added into spheronizer bowl
  Step 3: Spheronizer was run at 500 rpm to 800 rpm speed
  Step 4: 5 to 10 mL of water was added drop wise during the spheronization.
  Step 5: Pellets were further dried in hot air oven.

The formula composition for the ethyl cellulose coating for pellets is shown in Table 38 and the manufacturing procedure in Table 39.

TABLE 36

Formula composition for Ethyl cellulose coating

| Ingredients | % w/w weight gain | Quantity in g for 200 g batch size* |
|---|---|---|
| For 5% w/w ethyl cellulose coating (B. No. SF15000616) | | |
| Ethyl cellulose 20 standard premium | — | 9.6 g |
| Triethyl citrate | 25% | 2.4 g |
| IPA:Purified water | 1:1 | QS |

TABLE 36-continued

Formula composition for Ethyl cellulose coating

| Ingredients | % w/w weight gain | Quantity in g for 200 g batch size* |
|---|---|---|
| For 5% w/w ethyl cellulose coating (B. No. SF15000679) - PK batch | | |
| Ethyl cellulose 20 standard premium | — | 9.6 g |
| Triethyl citrate | 25% | 2.4 g |
| IPA:Purified water | 1:1 | QS |
| For 10% w/w ethyl cellulose coating (B. No. SF15000713) | | |
| Ethyl cellulose 20 standard premium | — | 19.2 g |
| Triethyl citrate | 25% | 4.8 g |
| IPA:Purified water | 1:1 | QS |
| For 5% w/w ethyl cellulose coating (B. No. SF15000775) - PK batch | | |
| Ethyl cellulose 20 standard premium | — | 9.6 g |
| Triethyl citrate | 25% | 2.4 g |
| IPA:Purified water | 1:1 | QS |

*20% overages in coating solution composition considered to compensate in process losses

TABLE 37

Manufacturing procedure for Ethyl cellulose coating

| Solution preparation | Machine Controls (GPCG 1.1 bottom spray) |
|---|---|
| Solution prepared for 5-10% w/w weight gain | Nozzle diameter - 0.8 mm |
| Overages considered for 20% w/w weight gain | Bottom Plate - Type C |
| Ethyl cellulose added into IPA: water solution with stirring | Inlet Temperature - 35° C.-50° C. |
| Triethyl citrate added into Ethyl cellulose solution | Product Temperature - 30° C.-40° C. |
| Solution is passed through ASTM 60# mesh before using it for coating | Exhaust Temperature - 40° C.-50° C. |

The ethyl cellulose coated sprinkles are further coated with Eudragit L 100 55 polymer for enteric protection. The formula composition for enteric coating is shown in Table 38 and the manufacturing procedure in Table 39.

TABLE 38

Formula composition for enteric coating

| Ingredients | % w/w weight gain | Quantity in grams for 200 g batch size[a] |
|---|---|---|
| For 30% w/w enteric coating (B. No. SF15000616) | | |
| Eudragit L 100 55 | — | 68.57[b] |
| Triethyl citrate | 25 | 17.15 |
| Talc | 50 | 34.27 |
| Acetone:IPA:Purified water (Diluent) | 38.1:57.13:4.77 | QS |
| For 40 and 50% w/w enteric coating (B. No. SF15000679)[c] | | |
| Eudragit L 100 55 | — | 68.57 |
| Triethyl citrate | 25 | 17.15 |
| Talc | 50 | 34.27 |
| Acetone:IPA:Purified water (Diluent) | 38.1:57.13:4.77 | QS |
| For 30, 40 and 50% w/w enteric coating (B. No. SF15000713)[d] | | |
| Eudragit L 100 55 | — | 68.57 |
| Triethyl citrate | 25 | 17.15 |
| Talc | 50 | 34.27 |
| Acetone:IPA:Purified water (Diluent) | 38.1:57.13:4.77 | QS |
| For 40% w/w enteric coating (B. No. SF15000775) | | |
| Eudragit L 100 55 | — | 54.86 |
| Triethyl citrate | 25 | 13.71 |
| Talc | 50 | 27.43 |
| Acetone:IPA:Purified water (Diluent) | 38.1:57.13:4.77 | QS |

[a]20% overages in coating solution composition considered to compensate in process losses
[b]coating solution was prepared for 50% w/w weight gain, however coating was done up to 30% w/w
[c]samples were collected after 40% w/w and batch continued to obtain 50% w/w sample
[d]samples were collected after 30%, 40% w/w and batch continued to obtain 50% w/w sample

TABLE 39

Manufacturing procedure for enteric coating

| Solution preparation | Machine Controls (GPCG 1.1 bottom spray) |
|---|---|
| Solution prepared for 50% W/W weight gain | Nozzle diameter - 1.2 mm |
| Overages considered for 20% W/W weight gain | Bottom Plate - Type C |
| Eudragit L100 55 was added into 50% of the diluent under stirring | Inlet Temperature - 25° C.-35° C. |
| Talc and Triethyl citrate were added into 50% of the diluent under Homogenizer | Product Temperature - 25° C.-30° C. |
| Homogenized suspension was added into Eudragit L 100 55 under stirring | Exhaust Temperature - 30° C.-40° C. |
| Solution is passed through ASTM 60# mesh before using it for coating | |

The Assay and dissolution results of Acamprosate calcium enteric-coated sprinkles are shown in Table 40.

TABLE 40

Assay and dissolution of acamprosate calcium pellets

Batch Number: SF154000616
Assay: 100.5% w/w
30% w/w enteric coated sprinkles (Eudragit L100 55)

| | Acid Stage pH 1.2 | Buffer Stage pH 6.8 | | | | |
|---|---|---|---|---|---|---|
| | 120 min | 30 min | 60 min | 90 min | 120 min | 180 min |
| 1 | 21 | 95 | 102 | 104 | 106 | 108 |
| 2 | 22 | 96 | 100 | 102 | 103 | 104 |
| 3 | 22 | 97 | 101 | 102 | 90 | 104 |
| AVG | 22 | 96 | 101 | 103 | 100 | 105 |

Batch Number: SF154000713
Assay: 100.3% w/w
10% w/w ethyl cellulose and 30% w/w enteric coated sprinkles

| | Acid Stage pH 1.2 | Buffer Stage pH 6.8 | | | | |
|---|---|---|---|---|---|---|
| | 120 min | 30 min | 60 min | 90 min | 120 min | 180 min |
| 1 | 18 | 60 | 68 | 80 | 85 | 91 |
| 2 | 14 | 55 | 67 | 77 | 82 | 90 |
| 3 | 15 | 55 | 67 | 76 | 83 | 88 |
| AVG | 16 | 57 | 67 | 78 | 83 | 90 |

TABLE 40-continued

Assay and dissolution of acamprosate calcium pellets

10% w/w ethyl cellulose and 40% w/w enteric coated sprinkles
Assay: 101.5% w/w

| | Acid Stage pH 1.2 | Buffer Stage pH 6.8 | | | | |
|---|---|---|---|---|---|---|
| | 120 min | 30 min | 60 min | 90 min | 120 min | 180 min |
| 1 | 9 | 51 | 64 | 71 | 75 | 83 |
| 2 | 8 | 48 | 63 | 69 | 75 | 83 |
| 3 | 10 | 52 | 66 | 72 | 76 | 83 |
| AVG | 9 | 50 | 64 | 71 | 75 | 83 |

10% w/w ethyl cellulose and 50% w/w enteric coated sprinkles
Assay: 100.7% w/w

| | Acid Stage pH 1.2 | Acid Stage pH 1.2 | | | | |
|---|---|---|---|---|---|---|
| | 120 min | 30 min | 60 min | 90 min | 120 min | 180 min |
| 1 | 6 | 50 | 64 | 70 | 80 | 84 |
| 2 | 6 | 46 | 60 | 69 | 76 | 86 |
| 3 | 6 | 52 | 63 | 72 | 76 | 86 |
| AVG | 6 | 49 | 62 | 70 | 77 | 85 |

Batch Number: SF15000679
5% w/w ethyl cellulose and 40% w/w enteric coated sprinkles

| | Acid Stage pH 1.2 | Buffer Stage pH 6.8 | | | | |
|---|---|---|---|---|---|---|
| | 120 min | 30 min | 60 min | 90 min | 120 min | 180 min |
| 1 | 6 | 30 | 91 | 90 | 101 | 104 |
| 2 | 8 | 79 | 95 | 98 | 103 | 106 |
| 3 | 9 | 81 | 95 | 100 | 103 | 105 |
| AVG | 8 | 63 | 94 | 96 | 102 | 105 |

5% w/w ethyl cellulose and 50% w/w enteric coated sprinkles

| | Acid Stage pH 1.2 | Buffer Stage pH 6.8 | | | | |
|---|---|---|---|---|---|---|
| | 120 min | 30 min | 60 min | 90 min | 120 min | 180 min |
| 1 | 4 | 82 | 75 | 97 | 97 | 104 |
| 2 | 4 | 72 | 82 | 94 | 96 | 101 |
| 3 | 4 | 71 | 85 | 92 | 95 | 98 |
| AVG | 4 | 75 | 81 | 94 | 96 | 101 |

Batch Number: SF15000775
Assay: 101.8% w/w
Coating percentage: 5% SR and 40% w/w Enteric-coated sprinkles

| | Acid Stage pH 1.2 | Buffer Stage pH 6.8 | | | | |
|---|---|---|---|---|---|---|
| | 120 min | 30 min | 60 min | 90 min | 120 min | 180 min |
| 1 | 11 | 78 | 89 | 94 | 96 | 100 |
| 2 | 11 | 82 | 92 | 97 | 101 | 99 |
| 3 | 11 | 78 | 89 | 94 | 97 | 99 |
| AVG | 11 | 79 | 90 | 95 | 98 | 99 |

The drug release of 30% in pH 1.2 buffer for enteric-coated sprinkles indicates that the 30% coating was not sufficient to control the drug release to <10%. Hence, a higher percentage of Eudragit coating, such as 40 to 50% enteric coating was considered.

Batch No: SF15000679

The drug release of 5% ethyl cellulose followed with 40% enteric coating sprinkles was found to be 8% in pH 1.2 and the drug release of 5% ethyl cellulose followed with 50% enteric coating was found to be 4% in pH 1.2. However, the drug release in buffer stage was found to be rapid.

Batch No: SF15000713

The drug release of 10% ethyl cellulose coating followed with 30%, 40% and 50% enteric coating was found to be 15%, 9% and 6%, respectively, in acid stage after 2 hours. Complete drug release was not observed for 10% ethyl cellulose coated pellets in buffer stage.

Based on these results, Batch No: SF15000679 (5% SR coating followed with 50% enteric coating) and Batch No: SF15000775 (5% SR coating and 40% enteric coating) were selected as PK batches.

Evaluation of Effect of Temperature on Drug Release

During the stability study for SF14000999, especially at 40° C./75% RH faster release of drug was observed with time in buffer stage. This was attributed/hypothesized to be due to migration of plasticizer to surface of ethyl cellulose coating layer and hence faster drug release at higher temperature. To evaluate the same quickly sprinkles were exposed in open petri plate for 2 weeks at 40° C./75% RH.

The pellets were directly added into a petri plate and covered with aluminum foil and pin holes to create open condition and stored at 40° C./75% RH. The dissolution results of initial and open petri plate study with different ethyl cellulose and Eudragit coating percentages is compiled in Table 41 and the profile is shown in FIG. 2-4.

TABLE 41

Dissolution results of sprinkles subjected to open petri plate study

| Batch description | % drug release at 120 min in pH 1.2 buffer | % drug release profile in pH 6.8 buffer | | | | | Complete release |
|---|---|---|---|---|---|---|---|
| | | 30 min | 60 min | 90 min | 120 min | 180 min | |
| 5% ethyl cellulose coating and 40% enteric coating (Initial) | 8 | 63 | 94 | 96 | 102 | 105 | |
| 5% ethyl cellulose coating and 40% enteric coating (2 weeks open petri plate study at 40° C./75% RH) | 5 | 80 | 87 | 97 | 101 | 102 | |
| 10% ethyl cellulose coating and 40% enteric coating (Initial) | 8 | 49 | 62 | 71 | 77 | 84 | 102 |
| 10% ethyl cellulose coating and 40% enteric coating (2 weeks open petri plate study at 40° C./75% RH) | 7 | 72 | 82 | 87 | 95 | 94 | 104 |
| 10% ethyl cellulose coating and 30% enteric coating (Initial) | 15 | 56 | 67 | 75 | 79 | 85 | 100 |

TABLE 41-continued

Dissolution results of sprinkles subjected to open petri plate study

| Batch description | % drug release at 120 min in pH 1.2 buffer | % drug release profile in pH 6.8 buffer | | | | | Complete release |
|---|---|---|---|---|---|---|---|
| | | 30 min | 60 min | 90 min | 120 min | 180 min | |
| 10% ethyl cellulose coating and 30% enteric coating (2 weeks open petri plate study at 40° C./75% RH) | 19 | 86 | 92 | 97 | 98 | 101 | |

The drug release of Acamprosate calcium pellets in acid stage found to be similar as compared to initial dissolution, which indicates that Eudragit coating is intact and has no influence on faster release. At 5% ethyl cellulose the release rate in buffer stage was similar both at initial and 2 week time point during open exposure. The drug release in buffer stage was found to be faster for 10% ethyl cellulose coating, indicating that higher ethyl cellulose percentage shows faster drug release at higher temperature.

Stability study of Acamprosate calcium pellets

The prototypes manufactured for PK supplies were loaded on stability and details are mentioned below:

Batch No.: SF15000679, SF15000775
Packaging: Sprinkles were weighed into aluminum sachets and sealed.
Fill weight: 874 mg sprinkles of batch number SF15000679
816 mg sprinkles of batch number SF15000775
(Sprinkles weighed are equivalent to 333 mg Acamprosate calcium)
Conditions: 25° C./60% RH & 40° C./75% RH
Time points: Initial, 1, 3, 6 & 12 months
Evaluation: Assay, related substances and dissolution The results of the stability study of sprinkles prototypes manufactured for PK study are summarized in Tables 42 and 43, and the dissolution profiles in FIGS. 5 and 6.

TABLE 42

Assay and dissolution results of Acamprosate calcium sprinkles at 40° C./75% RH

Batch Number - SF15000679 (Storage condition - 40° C./75% RH)

| | Time Interval | | | |
|---|---|---|---|---|
| | Initial | 1 Month | 3 Month | 6 Months |
| Assay (%) | 97.8 | 99.6 | 99.10 | 98.4 |

Dissolution

| Time | AVG (N = 3) | RSD (%) | AVG (N = 3) | RSD (%) | AVG (N = 3) | RSD (%) | AVG (N = 3) | RSD (%) |
|---|---|---|---|---|---|---|---|---|
| 120 min (pH 1.2 buffer) | 4 | 0 | 4 | 15.75 | 3 | 19.23 | 3 | 0.00 |

Dissolution in pH 6.8 buffer

| 30 min | 75 | 8.13 | 79 | 0.73 | 75 | 0.77 | 82 | 1.86 |
| 60 min | 81 | 6.30 | 89 | 0.65 | 85 | 1.80 | 93 | 4.17 |
| 90 min | 94 | 2.66 | 88 | 1.74 | 89 | 2.59 | 98 | 5.39 |
| 120 min | 96 | 1.04 | 96 | 0.60 | 91 | 4.44 | 101 | 0.66 |
| 180 min | 101 | 2.97 | 98 | 0.00 | 92 | 3.92 | 103 | 1.54 |

Batch Number - SF15000775 (Storage condition - 40° C./75% RH)

| | Time Interval | | | |
|---|---|---|---|---|
| | Initial | 1 Month | 3 Month | 6 Months |
| Assay (%) | 101.8 | 99.9 | 98.5 | 98.4 |

Dissolution

| Time | AVG (N = 3) | RSD (%) | AVG (N = 3) | RSD (%) | AVG (N = 3) | RSD (%) | AVG (N = 3) | RSD (%) |
|---|---|---|---|---|---|---|---|---|
| 120 min (pH 1.2 buffer) | 11 | 0 | 7 | 14.29 | 5 | 0.00 | 3 | 0.0 |

Dissolution in pH 6.8 buffer

| 30 min | 79 | 2.92 | 82 | 1.87 | 84 | 4.12 | 82 | 2.53 |
| 60 min | 90 | 1.92 | 93 | 2.15 | 95 | 1.61 | 93 | 4.17 |
| 90 min | 95 | 1.82 | 99 | 3.26 | 99 | 0.58 | 95 | 5.39 |
| 120 min | 98 | 2.7 | 100 | 2.07 | 100 | 1.16 | 99 | 0.66 |
| 180 min | 99 | 0.58 | 103 | 1.49 | 104 | 2.78 | 101 | 1.54 |

TABLE 43

Assay and dissolution results of Acamprosate calcium sprinkles at 25° C./60% RH

Batch Number - SF15000679 (Storage condition - 25° C./60% RH)

| | Time Interval | | | | |
|---|---|---|---|---|---|
| | Initial | 1 Month | 3 Months | 6 Months | 12 Months |
| Assay (%) | 97.8 | 100.8 | 96 | 96.6 | |

| | Dissolution | | | | | | | | | |
|---|---|---|---|---|---|---|---|---|---|---|
| Time | AVG (N = 3) | RSD (%) | AVG (N = 3) | RSD (%) | AVG (N = 3) | RSD (%) | AVG (N = 3) | RSD (%) | AVG (N = 3) | RSD (%) |
| 120 min (pH 1.2 buffer) | 3 | 0 | 3 | 17.32 | 2.0 | 28.85 | 3 | 0.0 | | |
| Dissolution in pH 6.8 buffer | | | | | | | | | | |
| 30 min | 75 | 8.13 | 69 | 7.67 | 71 | 0.81 | 73 | 7.25 | | |
| 60 min | 81 | 6.30 | 81 | 4.45 | 85 | 0.68 | 83 | 4.17 | | |
| 90 min | 94 | 2.66 | 92 | 0.63 | 90 | 0.0 | 85 | 5.39 | | |
| 120 min | 96 | 1.04 | 92 | 1.09 | 92 | 0.63 | 88 | 0.66 | | |
| 180 min | 101 | 2.97 | 94 | 1.06 | 95 | 0.61 | 99 | 1.54 | | |

Batch Number - SF15000775 (Storage condition - 25° C./60% RH)

| | Time Interval | | | | |
|---|---|---|---|---|---|
| | Initial | 1 Month | 3 Months | 6 Months | 12 Months |
| Assay (%) | 101.8 | 97.75 | 98.20 | 98.90 | |

| | Dissolution | | | | | | | | | |
|---|---|---|---|---|---|---|---|---|---|---|
| Time | AVG (N = 3) | RSD (%) | AVG (N = 3) | RSD (%) | AVG (N = 3) | RSD (%) | AVG (N = 3) | RSD (%) | AVG (N = 3) | RSD (%) |
| 120 min (pH 1.2 buffer) | 11 | 0.00 | 9 | 0.00 | 7 | 8.24 | 3 | 0.00 | | |
| Dissolution in pH 6.8 buffer | | | | | | | | | | |
| 30 min | 79 | 2.92 | 81 | 1.42 | 82 | 7.69 | 89 | 1.12 | | |
| 60 min | 90 | 1.92 | 92 | 1.65 | 90 | 0.64 | 98 | 4.17 | | |
| 90 min | 95 | 1.82 | 99 | 2.10 | 96 | 0.60 | 102 | 5.39 | | |
| 120 min | 98 | 2.7 | 101 | 0.57 | 98 | 1.02 | 100 | 0.66 | | |
| 180 min | 99 | 0.58 | 103 | 1.06 | 99 | 1.17 | 103 | 1.54 | | |

Acamprosate calcium sprinkles manufactured with 5% ethyl cellulose and 40% to 50% eudragit coating were found to meet the target product attributes and also were found to be stable for a period of 6 months.

2. Dog Studies a. Capral Study

Pharmacokinetic study '537 was conducted in beagle dogs at Covance's Madison, Wis. facility. This accepted animal model is used to understand how our drug's active ingredient would be absorbed, distributed and eliminated. It should be noted that beagle dogs were used as the animal model for Campral and published research is available for comparison (Kathleen Haberny-FDA Review, Adam Wasserman-FDA review and Rhee et al., 2008 a, b). Study '537 allowed us to demonstrate the baseline profile for the existing 333 mg enteric-coated tablet across several dose ranges, and at the same time compare a simple "naked" formulation with no excipients where the active ingredient was dissolved in an aqueous solution.

The studies confirmed three findings; the initial peak concentration (Cmax) of the active drug in the body increased substantially though deliver as a non-enteric coated solution, second the amount of "naked" drug systemically available (bioavailability) was considerably higher than the Campral tablet, and lastly, a "naked" drug substantially increased G.I. intolerability across all dosages for all dogs. The completed formulation study demonstrated the challenges of a simple, "naked" aqueous solution was impractical path for administering this drug.

b. Acamprosate Calcium Enteric-Coated Sprinkles: (1st Generation Studies)

The following target product profile for two pediatric-friendly formulation technologies was developed which could meet the special needs of the Fragile X Syndrome patient population which experiences difficulties taking pills due to oral fixation issues (chewing, gagging and inability to swallow) as well as sensitivities to color, texture and taste while accommodating the challenges of this BCS III compound. Two dosage forms were contemplated in the target product profile for acamprosate calcium; a micro-sized particle and small-particle Sprinkle form, as described in Table 44.

TABLE 44

| | |
|---|---|
| API Name | Acamprosate calcium |
| Dosage Form | Small particle Sprinkle dosage form in sachet Micro-sized particle to be constituted with water to obtain uniform suspension. |
| Dosage strengths | Granules equivalent to 300 mg in sachet - for apple sauce, yogurt, pudding 300 mg/5 ml (600 b.i.d) - after constitution in bottle |
| Packaging | Single dose Sachet or HDPE bottle |
| Drug Product Stability Program | Informal stability of prototypes 40° C./75% RH - Initial, 1M, 3M and 6M 25° C./60% RH - 1M, 3M and 6M |
| Analytical Method Requirements | Assay and related substances (by HPLC), Dissolution |
| Deliverable | Supply 1-2 prototypes for further development |

Formulation development activities included preformulation profiling, drug excipient compatibility studies, drug product methods development, formulation development and informal stability of developed formulations. A number of micro-size particle prototypes were rendered using by several different methodologies with no prototype meeting the target product profile. The development team was unable to consistently coat the API microparticles to delay dissolution.

As an alternative formulation approach, the development team considered sprinkles/pellets uniformly coated with sustained release polymers and enteric coated polymers. With experience from the micro-size particle formulation effort, the development team designed several sprinkle prototypes with dissolution characteristics matched the TPP in both acid (pH=1.2) and buffer (pH=6.8) stages. Since the prototypes were intended to be administered in an edible matrix such as applesauce, pudding or yogurt, dissolution studies were also conducted in pH ranges consistent with those matrices. From those development activities prototype SF14000999 appeared to meet the target product profile.

The development of SF14000999 was advanced to dog study '752 where the team analyzed the PK and Tolerability profile of SF14000999 in comparison with Campral tablet. This 7 day study dosed the dogs daily at 1,332 mg BID for an aggregate exposure of 2,664 mg per day. All dogs were male non-naïve beagle dogs from the Covance stock colony. At dosing, the animals weighed 9.4 to 12.0 kg and were young adult/adult. Animals were identified with individually numbered cage cards or an implantable microchip identification device (IMID). Animals were selected for test based on overall health and body weight. The study was conducted under fed conditions and animals were given Certified Canine Diet #5007 and food was provided ad libitum. Water was provided fresh daily ad libitum. Animals were housed in stainless steel cages in a room set to maintain a temperature of 20 to 26° C., a relative humidity of 50±20%, and a 12-hour light/12-hour dark cycle. As necessary, the 12-hour dark cycle was temporarily interrupted to accommodate study procedures. Sprinkles were filled into rapidly dissolving capsules at Covance and portioned out for twice-daily administration throughout the dosing period. Campral tablets were administered twice-daily throughout the dosing period. Any remaining tablets or filled capsules were stored at ambient temperature. Individual doses were orally administered as a fixed dose of 4 capsules/tablets per animal (1332 mg per animal) twice daily, approximately 12 hours apart, for a total dose of 8 capsules/tablets per day (2664 mg per animal) followed by approximately 10 mL of water.

Twice daily (a.m. and p.m.), animals were observed for mortality and signs of pain and distress. Cageside observations for general health and appearance were done once daily. Any unusual observations noted throughout the duration of the study were recorded in the raw data. Body weights were taken at the time of animal selection and on Day 1 of dose administration. On Days 1 and 7, blood (approximately 2 mL) was collected from a jugular vein into tubes containing $K_2$EDTA anticoagulant predose and at 0.25, 0.5, 1, 2, 4, 8, 12, 24, and 48 (Day 7 only) hours postdose. The 12-hour blood samples were collected prior to the 12-hour dose and the 24-hour blood samples were collected prior to the Day 2 dose.

The results of the study demonstrated high variability, GI disturbance in all dogs (with non-formed or liquid feces) and the presence of sprinkles in the feces of all dogs in the group. FIG. 7 shows the Day 1 PK for this study during the first 12 hour period.

A second dog study '326 was conducted to determine if the very high drug exposure for SF14000999 was the cause of the GI disturbance and further causing insufficient time for the sprinkles to release. Study '326 compared SF14000999 and Campral dosed at 666 mg BID for an aggregate daily exposure of 1,332 mg. The protocol was kept relatively the same with the following exceptions; the study was shortened to 4 days and the dose was lessen to 1,332 mg per day. Individual doses were administered as a fixed dose of 2 capsules/tablets per animal (666 mg per animal) twice daily, approximately 12 hours apart, for a total dose of 4 capsules/tablets per day (1332 mg per animal). The capsule/tablet doses were administered orally, followed by approximately 10 mL of water.

Twice daily (a.m. and p.m.), animals were observed for mortality and signs of pain and distress. Cageside observations for general health and appearance were done once daily. Any unusual observations noted throughout the duration of the study were recorded in the raw data. Following each cageside observation, feces were removed from the cage and discarded. Selected fecal samples were retained and photographed for informational purposes only. Body weights were taken at the time of animal selection and on Day 1 of dose administration. On Day 1, blood (approximately 2 mL) was collected via a jugular vein from each animal into tubes containing $K_2$EDTA anticoagulant predose and at 0.25, 0.5, 1, 2, 4, 8, 12 (prior to next dose), 13, 16, 20, and 24 hours postdose.

FIG. 8 shows the Day 1 PK for the 666 mg BID study. The data demonstrated that the exposures (Cmax/AUC) were lower for sprinkle prototype SF14000999 than Campral. The sprinkles demonstrated a delayed onset (Tmax 13.5 hrs) relative to Campral (Tmax 4.7 hrs). We concluded from Studies 8321752 and 8326326 that the SF14000999 prototype was not suitable and needed further refinement to improve and meet desired targeted product PK and tolerability characteristics.

c. Acamprosate Calcium Enteric-Coated Sprinkles: ($2^{nd}$ Generation Studies)

With the learnings from prototype SF14000999, two new formula prototypes were developed: SF15000679 and SF15000775. Both new prototypes demonstrated favorable release profiles as compared to Campral and SF14000999. By lessening the plasticizer and enteric coatings for both sprinkle formulas, SF15000679 and SF15000775 resulted in a higher drug loads per sprinkle particle while maintaining the same or lesser particle size.

Figure 10:
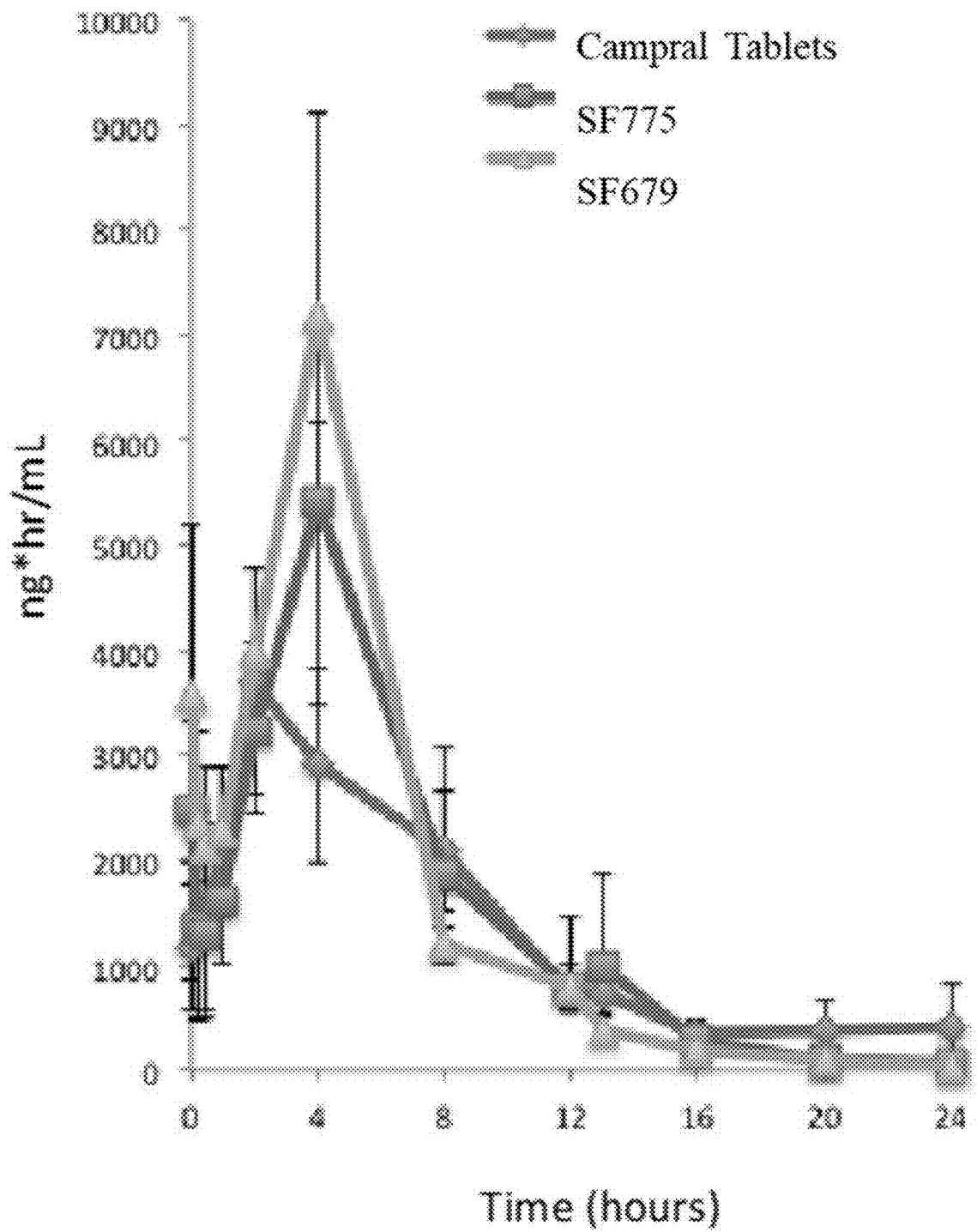
FIG. 10 shows PK-1332 mg (666 mg BID) Day 1 vs. Day 4—Campral vs. SF15000679 vs. SF15000775.

Replicating the same basic protocol from dog study '326, the PK and Tolerability study comparing the two new prototypes with the enteric coated Campral tablets was repeated. Once again, this was a 4-day study with days 1-3 dosed 666 mg BID (aggregate of 1,332 mg/day) and day 4 was a single 666 mg morning dose. The PK-1332 mg (666 mg BID) Day 1 results are shown in FIG. 9, while the PK-1332 mg (666 mg BID) Day 1 vs. Day 4 results are shown in FIG. 10. The results are tabulated in Table 45.

TABLE 45

| | Tmax (hr) | Cmax (ng/mL) | AUC0-12 (hr * ng/ml) | AUC 12-24 (hr * ng/ml) | AUC Last (hr * ng/ml) |
|---|---|---|---|---|---|
| DAY 1 | | | | | |
| Campral Tablets | 6.0 | 5060 | 16100 | 16200 | 32300 |
| SF775 | 9.0 | 4900 | 16700 | 27900 | 44700 |
| SF679 | 11.3 | 6040 | 31600 | 25700 | 57300 |
| DAY 4 | | | | | |
| Campral Tablets | 2.0 | 4020 | 26700 | | 32200 |
| SF775 | 3.5 | 5480 | 32500 | | 36400 |
| SF679 | 4.0 | 7180 | 37500 | | 39800 |

The results of this study demonstrated that both new sprinkle prototypes showed increased exposure relative to SF14000999. The Tmax of SF15000679 delayed slightly compared to SF15000775 and the Campral tablets. Bioavailability increased by 77% for SF15000679 relative to Campral tablets. In summary, dog PK and tolerability studies for prototypes SF15000679 and SF15000775 demonstrated to have superior release characteristics and higher bioavailability in comparison to SF14000999 and Campral.

The invention claimed is:

1. An orally-administrable, pharmaceutical formulation comprising a plurality of pellets, wherein:
   the pellets comprise a core, a sustained release coating, and an enteric coating; and
   the core comprises acamprosate calcium and a diluent.
2. The pharmaceutical formulation of claim 1, wherein the diluent comprises a microcrystalline cellulose or a cellulose gel.
3. The pharmaceutical formulation of claim 2, wherein the diluent comprises a microcrystalline cellulose.
4. The pharmaceutical formulation of claim 1, wherein the sustained release coating comprises a thermoplastic cellulose ether.
5. The pharmaceutical formulation of claim 4, wherein the sustained release coating comprises ethyl cellulose standard 20.
6. The pharmaceutical formulation of claim 1, wherein the enteric coating comprises an anionic copolymer comprising a reaction product of methacrylic acid and ethyl acrylate.
7. The pharmaceutical formulation of claim 6, wherein the enteric coating comprises an anionic copolymer based on about 1:1 methacrylic acid and ethyl acrylate.
8. The pharmaceutical formulation of claim 1, wherein the plurality of pellets range in size from about 0.5 mm to about 3.1 mm.
9. The pharmaceutical formulation of claim 1, wherein the plurality of pellets range in size from about 0.6 mm to about 1.5 mm, as measured using a ASTM Mesh.
10. The pharmaceutical formulation of claim 1, wherein acamprosate calcium is homogeneously dispersed in the plurality of pellets.
11. The pharmaceutical formulation according to claim 1, wherein the acamprosate calcium comprises about 5 to about 60 w/w % of the core.
12. The pharmaceutical formulation of claim 1, wherein the acamprosate calcium comprises about 45 to about 65 w/w % of the core.
13. The pharmaceutical formulation of claim 12, wherein the acamprosate calcium comprises about 50 to about 60 w/w % of the core.
14. The pharmaceutical formulation of claim 1, wherein the plurality of pellets is contained in a sachet or capsule.
15. The pharmaceutical formulation of claim 14, wherein the sachet contains a unit dose of acamprosate calcium.
16. The pharmaceutical formulation of claim 15, wherein the unit dose is about 100 mg to about 2500 mg.
17. A method of treating a medical condition in a patient, the method comprising administering to the patient an effective amount of the pharmaceutical formulation of claim 1.
18. The method of claim 17, wherein the medical condition is age-related cognitive impairment, Mild Cognitive Impairment (MCI), dementia, Alzheimer's Disease (AD), prodromal AD, post traumatic stress disorder (PTSD), schizophrenia, bipolar disorder, amyotrophic lateral sclerosis (ALS), cancer-therapy-related cognitive impairment, drug induced or toxin induced cognitive impairment, mental retardation, Parkinson's disease (PD), levodopa-induced dyskinesias in Parkinson's Disease, autism, Autism Spectrum Disorder, Pervasive Development Disorder-Not Otherwise Specified, Idiopathic Autism, Fragile X Syndrome, Asperger's Syndrome, Rhett's Syndrome, or Childhood Disintegrative Disorder compulsive behavior, tinnitus, sleep apnea, Cortical spreading depression, migraine, anxiety, tardive dyskinesia, spasticity, multiple sclerosis, pain, binge eating, alcohol dependence, or substance addiction.
19. The method of claim 17, wherein the medical condition is Fragile X syndrome.
20. The method of claim 17, wherein the medical condition is a neurotransmission or cognitive disorder characterized as a glutamate-GABA imbalance, or a disorder characterized with disrupted or dysregulated ERK signaling pathway or rasopathies resulting in abnormalities in brain development, learning, memory or cognition.

* * * * *